United States Patent
Wu et al.

(10) Patent No.: US 11,337,612 B2
(45) Date of Patent: May 24, 2022

(54) METHOD AND SYSTEM FOR WOUND ASSESSMENT AND MANAGEMENT

(71) Applicant: CHILDREN'S NATIONAL MEDICAL CENTER, Washington, DC (US)

(72) Inventors: Kyle Wu, Arlington, VA (US); Peng Cheng, Fairfax, VA (US); Peter Kim, Washington, DC (US); Ozgur Guler, Falls Church, VA (US)

(73) Assignee: CHILDREN'S NATIONAL MEDICAL CENTER, Washington, DC (US)

( * ) Notice: Subject to any disclaimer, the term of this patent is extended or adjusted under 35 U.S.C. 154(b) by 0 days.

(21) Appl. No.: 14/491,794

(22) Filed: Sep. 19, 2014

(65) Prior Publication Data
US 2015/0150457 A1 Jun. 4, 2015

Related U.S. Application Data

(60) Provisional application No. 61/983,022, filed on Apr. 23, 2014, provisional application No. 61/911,162, filed on Dec. 3, 2013.

(51) Int. Cl.
*A61B 5/00* (2006.01)
*G06T 7/00* (2017.01)
(Continued)

(52) U.S. Cl.
CPC .......... *A61B 5/0077* (2013.01); *A61B 5/0073* (2013.01); *A61B 5/445* (2013.01);
(Continued)

(58) Field of Classification Search
CPC ..... A61B 5/0077; A61B 5/0073; A61B 5/445; A61B 5/6898; A61B 5/0022;
(Continued)

(56) References Cited

U.S. PATENT DOCUMENTS

| 5,967,979 A | * 10/1999 | Taylor ................. A61B 5/0059 356/613 |
| 6,081,612 A | 6/2000 | Gutkowicz-Krusin et al. |

(Continued)

FOREIGN PATENT DOCUMENTS

JP 2010-504108 A 2/2010

OTHER PUBLICATIONS

International Search Report dated Dec. 30, 2014 in International Application No. PCT/US2014/056587.
(Continued)

*Primary Examiner* — Jonathan Cwern
(74) *Attorney, Agent, or Firm* — Oblon, McClelland, Maier & Neustadt, L.L.P.

(57) ABSTRACT

Described herein is a system and method for determining characteristics of a wound. The system includes a first imaging sensor that obtains imaging information of a wound area and a second imaging sensor that obtains topology information of the wound area. The system further includes circuitry that designates a representative background portion of the wound area from the imaging information of the wound area, that designates a representative wound portion of the wound area from the imaging information of the wound area, that determines the boundary of the wound portion within the imaging information of the wound area based on the designated representative background and wound portions, that correlates the imaging information and the topology information, that applies the boundary of the wound portion designated within the imaging information to the topology information to designate a mask area, and that determines characteristics of the wound portion within the mask area based on the topology information and the imaging information.

34 Claims, 13 Drawing Sheets

(51) Int. Cl.
*G06T 7/12* (2017.01)
*G06T 7/62* (2017.01)
*G16H 30/40* (2018.01)
*A61B 5/107* (2006.01)

(52) U.S. Cl.
CPC .......... *A61B 5/6898* (2013.01); *G06T 7/0012* (2013.01); *G06T 7/12* (2017.01); *G06T 7/62* (2017.01); *G16H 30/40* (2018.01); *A61B 5/0022* (2013.01); *A61B 5/1077* (2013.01); *A61B 5/1079* (2013.01); *A61B 2576/02* (2013.01); *G06T 2207/10028* (2013.01); *G06T 2207/30088* (2013.01); *G06T 2207/30096* (2013.01)

(58) Field of Classification Search
CPC . A61B 5/1077; A61B 5/1079; A61B 2576/02; G06T 7/0012; G06T 7/12; G06T 7/62; G06T 2207/10028; G06T 2207/30088; G06T 2207/30096; G16H 30/40; G16H 30/00
See application file for complete search history.

(56) References Cited

U.S. PATENT DOCUMENTS

| | | | | |
|---|---|---|---|---|
| 6,081,739 | A * | 6/2000 | Lemchen | A61B 5/0064 600/407 |
| 2008/0045807 | A1 | 2/2008 | Psota et al. | |
| 2008/0071161 | A1 | 3/2008 | Jaeb et al. | |
| 2008/0075343 | A1 * | 3/2008 | John | A61B 6/541 382/131 |
| 2008/0226151 | A1 | 9/2008 | Zouridakis et al. | |
| 2008/0260221 | A1 | 10/2008 | Unal et al. | |
| 2010/0172567 | A1 * | 7/2010 | Prokoski | A61B 5/0064 382/132 |
| 2012/0078113 | A1 * | 3/2012 | Whitestone | A61B 5/0077 600/474 |
| 2012/0115138 | A1 | 5/2012 | Deigner et al. | |
| 2013/0053677 | A1 | 2/2013 | Schoenfeld | |

OTHER PUBLICATIONS

Uma Maheswari R., et al., "Interactive Liver Tumor Segmentation Using Graph Cut and Grab Cut", International Journal of Research in Engineering and Technology, vol. 2; Issue 10, Oct. 2013, pp. 609-614.
Office Action dated Mar. 24, 2017 in European Patent Application No. 14868672.8.
Extended European Search Report dated Mar. 7, 2017 in Patent Application No. 14868672.8.
Japanese Office Action dated May 29, 2018 in Patent Application No. 2016-536570, 4 pages.
Office Action dated May 25, 2019, in Australia Patent Application No. 2014357720, 3 pgs.
Office Action dated Jan. 8, 2019, in Japanese Patent Application No. 2016-536570 (with English-language translation) (6 pages).
Office Action dated Aug. 5, 2019 in People's Republic of China patent application No. 201480070811.7 (w/English-language translation); 24 pgs.
Office Action dated Dec. 4, 2018, in China Patent Application No. 201480070811.7 (with English-language translation); 24 pgs.
Uma Maheswari R. et al.; "Interactive Liver Tumor Segmentation Using Graph Cut and Grab Cut"; IJRET: International Journal of Research in Engineering and Technology; EISSN: 2319-1163/ PISSN: 2321-7308; 6 pgs.
Australian Examination Report dated Jan. 21, 2020, in Patent Application No. 2014357720, 4 pages.
Office Action dated Feb. 7, 2020 in Indian Application No. 201617016442, 8 pages.
Full Examination Report dated Mar. 4, 2020 in Australian Application No. 2014357720, 4 pages.
Office Action dated Nov. 20. 2019 in Europe Patent Application No. 14 888 672.8-1115, (9 pages).
Office Action dated Sep. 28, 2021 in Canada Patent Application No. 2,930,184; 3 pgs.

* cited by examiner

METHOD AND SYSTEM FOR WOUND ASSESSMENT AND MANAGEMENT

CROSS-REFERENCE TO RELATED APPLICATIONS

This application is based upon and claims the benefit of priority under 35 U.S.C. § 119(e) from U.S. Ser. No. 61/911,162, filed Dec. 3, 2013, and U.S. Ser. No. 61/983,022, filed Apr. 23, 2014, the entire contents of each of which are incorporated herein by reference.

BACKGROUND

Chronic and complex wounds, including venous, diabetic, and pressure ulcers, surgical wounds, ostomy and other complex wounds affect millions of patients in the United States alone. Billions of dollars are spent on the treatment of chronic wounds in the United States annually, including over billions on wound care products. The cost of treating chronic wounds continues to grow year after year due to an aging population and rising incidence of diabetes and obesity. The treatment cost for chronic wound has become a significant financial burden to the individual and society.

While advances in medical technology have helped bring new treatment modalities to the various wound types, there is a large unmet need for accurate and objective assessment of a wound and the wound healing progress, including wound depth, volume, area, circumference measurements and classification of the wound. Objective assessment of wound healing progress is the basis for determining the effectiveness of a treatment pathway, and critical in selecting the best treatment plan. However, in the clinical setting, such measurements are usually inaccurate, subjective, and inconsistent (performed manually with ruler, transparency tracing, and Q-tips for depth). Because of the lack of standards and reliability, these measurements are often difficult to apply to clinical practice for medical decision making. Furthermore, the inconsistencies in wound assessment also render remote management or multidisciplinary wound care coordination difficult to implement. To address this issue, many wound measurement tools have been developed using structured light and stereo-photography. These systems, however, require specialized/expensive equipment, which is difficult to use, lack integration with medical record management systems, and are overall inefficient at accurately assessing a wound. As a result, these wound measurement tools are not practical in point-of-care settings.

Another unmet need in wound and many other disease management areas (including but not limited to dermatology, aesthetics, cosmetics, oncology, ophthalmology, and otolaryngology) is the growing need for an efficient, secure, and collaborative system for managing visual and other multimedia information.

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein.

DETAILED DESCRIPTION

Figure 1:
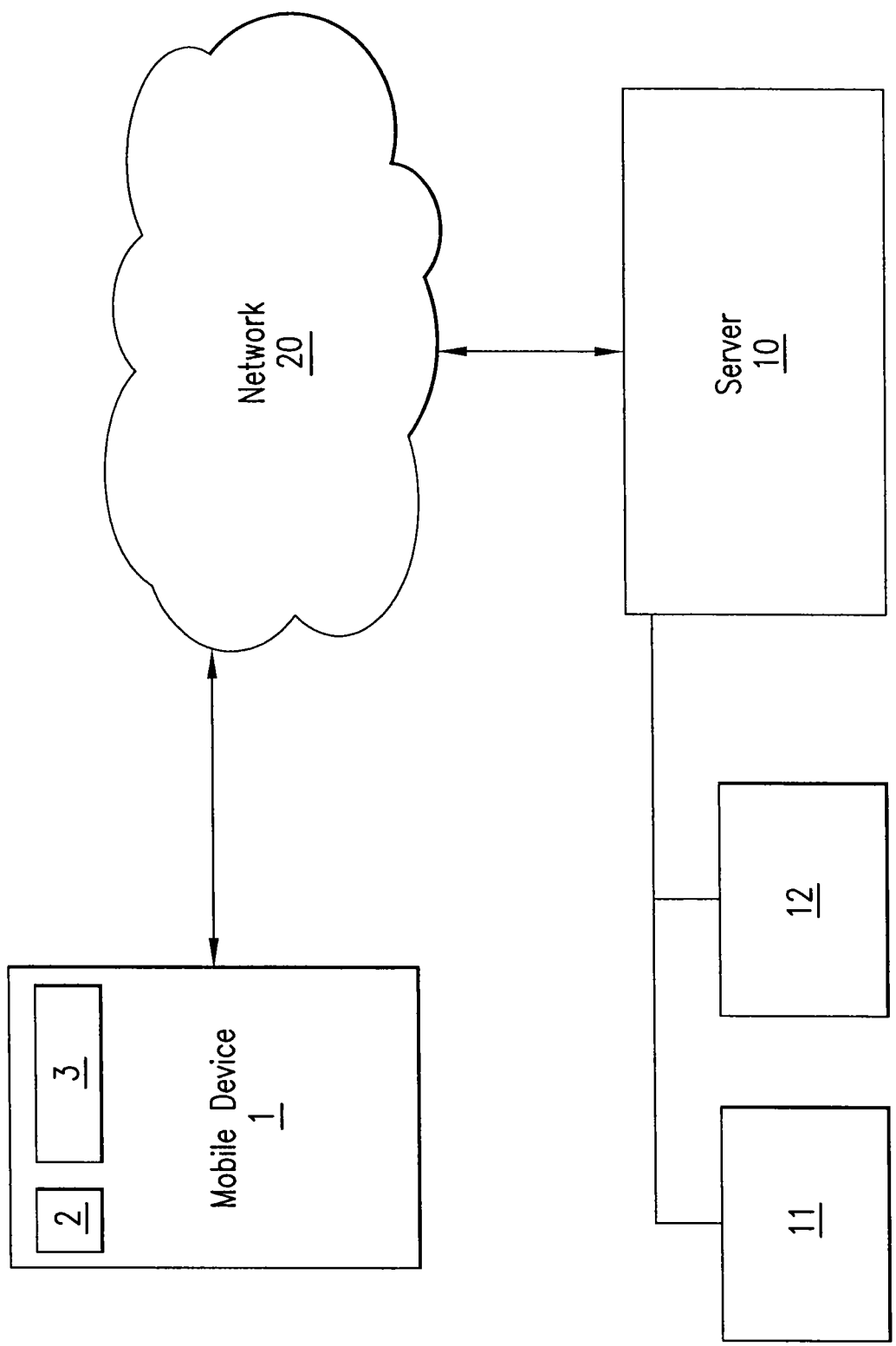
FIG. 1 illustrates an example of a system diagram according to one embodiment.

The present disclosure describes system for determining characteristics of a medical injury. The system includes one or more imaging sensors that obtain imaging information and topology information of an area of interest, and circuitry configured to determine a boundary of an injury portion within the imaging information of the area of interest, correlate the imaging information and the topology information, apply the boundary of the injury portion designated within the imaging information to the topology information to designate a mask area, and determine characteristics of the injury portion within the mask area based on the topology information and the imaging information.

The system further includes an embodiment in which the circuitry is further configured to designate a representative background portion of the area of interest from the imaging information of the area of interest, designate a representative injury portion of the area of interest from the imaging information of the area of interest, and determine the boundary of the injury portion within the imaging information of the area of interest based on the designated representative background and injury portions.

The system further includes an embodiment in which the circuitry is further configured to designate a representative injury portion of the area of interest from the imaging information of the area of interest based on user input or pixel characteristic differences.

The system further includes an embodiment in which the circuitry is further configured to classify the injury portion within the mask area based on the imaging information.

The system further includes an embodiment in which the circuitry is further configured to classify the injury portion within the mask area by being configured to divide the injury portion into tiles, to calculate a measure of central tendency for imaging values of each tile, and to classify each tile using injury type information generated by a previously trained classifier.

The system further includes an embodiment in which the injury type information includes healthy, slough, and eschar tissue.

The system further includes an embodiment in which the previously trained support vector machine generates the injury type information using circuitry configured to, for a set of annotated images, divide each image into tiles, to calculate a measure of central tendency for imaging values of each tile, to designate each tile according to an injury type, and to apply cross-validation using a separate test set.

The system further includes an embodiment in which the characteristics of the injury portion within the mask area include depth, width, and length of the injury.

The system further includes an embodiment in which the characteristics of the injury portion within the mask area include perimeter, area, and volume of the injury.

The system further includes an embodiment in which the circuitry is configured to determine the boundary of the injury portion within the imaging information of the area of interest by utilizing an automatic image segmentation algorithm.

The system further includes an embodiment in which the circuitry is configured to determine the boundary of the injury portion within the imaging information of the area of interest by detecting contours in the representative injury portion of the area of interest.

The system further includes an embodiment in which the circuitry is configured to determine the boundary of the injury portion within the imaging information of the area of interest by detecting contours in the representative injury portion of the area of interest and iterating over all contours.

The system further includes an embodiment in which the medical injury is a wound.

Further described is an embodiment of a device for determining characteristics of a medical injury. The device includes circuitry configured to determine a boundary of an injury portion within imaging information of an area of interest, correlate the imaging information and topology information obtained by one or more imaging sensors, apply the boundary of the injury portion designated within the imaging information to the topology information to designate a mask area, and determine characteristics of the injury portion within the mask area based on the topology information and the imaging information.

The device further includes an embodiment in which the circuitry is further configured to designate a representative background portion of the area of interest from the imaging information of the area of interest, designate a representative injury portion of the area of interest from the imaging information of the area of interest, and determine the boundary of the injury portion within the imaging information of the area of interest based on the designated representative background and injury portions.

The device further includes an embodiment in which the circuitry is further configured to designate a representative injury portion of the area of interest from the imaging information of the area of interest based on user input or pixel characteristic differences.

The device further includes an embodiment in which the circuitry is further configured to classify the injury portion within the mask area based on the imaging information.

The device further includes an embodiment in which the circuitry is further configured to classify the injury portion within the mask area by being configured to divide the injury portion into tiles, to calculate a measure of central tendency for imaging values of each tile, and to classify each tile using injury type information generated by a previously trained support vector machine.

The device further includes an embodiment in which the injury type information includes healthy, slough, and eschar tissue.

The device further includes an embodiment in which the previously trained support vector machine generates the injury type information using circuitry configured to, for a set of annotated images, divide each image into tiles, to calculate a measure of central tendency for imaging values of each tile, to designate each tile according to a injury type, and to apply cross-validation using a separate test set.

The device further includes an embodiment in which the characteristics of the injury portion within the mask area include depth, width, and length of the injury.

The device further includes an embodiment in which the characteristics of the injury portion within the mask area include perimeter, area and volume of the injury.

The device further includes an embodiment in which the circuitry is configured to determine the boundary of the injury portion within the imaging information of the area of interest by utilizing a grab cut algorithm.

The device further includes an embodiment in which the circuitry is configured to determine the boundary of the injury portion within the imaging information of the area of interest by detecting contours in the representative injury portion of the area of interest.

The device further includes an embodiment in which the circuitry is configured to determine the boundary of the injury portion within the imaging information of the area of interest by detecting contours in the representative injury portion of the area of interest and iterating over all contours.

The device further includes an embodiment in which the medical injury is a wound.

Also described is an embodiment of a method for determining characteristics of a medical injury. The method includes the steps of determining, using processing circuitry, a boundary of an injury portion within imaging information of an area of interest, correlating, using the processing circuitry, the imaging information and topology information obtained by one or more imaging sensors, applying, using the processing circuitry, the boundary of the injury portion designated within the imaging information to the topology information to designate a mask area, and determining, using the processing circuitry, characteristics of the injury portion within the mask area based on the topology information and the imaging information.

The method further includes an embodiment including the further steps of designating a representative background portion of the area of interest from the imaging information of the area of interest, designating a representative injury portion of the area of interest from the imaging information of the area of interest, and determining the boundary of the injury portion within the imaging information of the area of interest based on the designated representative background and injury portions.

The method further includes an embodiment including the further step of designating a representative injury portion of the area of interest from the imaging information of the area of interest based on user input or pixel characteristic differences.

The method further includes an embodiment including the further step of classifying the injury portion within the mask area based on the imaging information.

The method further includes an embodiment in which the further step of the injury portion within the mask area is further classified by dividing the injury portion into tiles, to calculate a measure of central tendency for imaging values of each tile, and to classify each tile using injury type information generated by a previously trained support vector machine.

The method further includes an embodiment in which the injury type information includes healthy, slough, and eschar tissue.

The method further includes an embodiment in which the previously trained support vector machine generates the injury type information using circuitry configured to, for a set of annotated images, divide each image into tiles, to calculate a measure of central tendency for imaging values of each tile, to designate each tile according to an injury type, and to apply cross-validation using a separate test set.

The method further includes an embodiment in which the characteristics of the injury portion within the mask area include depth, width, and length of the injury.

The method further includes an embodiment in which the characteristics of the injury portion within the mask area include perimeter, area and volume of the injury.

The method further includes an embodiment including the further step of determining the boundary of the injury portion within the imaging information of the area of interest by utilizing a grab cut algorithm.

The method further includes an embodiment including the further step of determining the boundary of the injury portion within the imaging information of the area of interest by detecting contours in the representative injury portion of the area of interest.

The method further includes an embodiment including the further step of determining the boundary of the injury portion within the imaging information of the area of interest by detecting contours in the representative injury portion of the area of interest and iterating over all contours.

The method further includes an embodiment in which the medical injury is a wound.

Referring now to the drawings wherein like reference numbers designate identical or corresponding parts throughout the several views, FIG. 1 illustrates a system for the volumetric assessment of chronic and complex wounds, such as but not limited to pressure ulcers, diabetic ulcers, arterial insufficiency ulcers, venous stasis ulcers, and burn wounds. Chronic wounds often require constant monitoring and attention. Beyond the visual information that can be obtained by a traditional single 2D camera, the three dimensional surface data is of particular clinical relevance. Thus, the capturing, analysis, and transmission of clinical data and imagery using mobile devices, a specialized camera with structured sensor capability, and a cloud/network infrastructure, can provide significant improvements over existing technology. The present embodiments incorporate the above components to provide a complete platform to capture, evaluate, document, and communicate clinical information for the purpose of wound prevention and treatment.

FIG. 1 illustrates system diagram according to an embodiment. In FIG. 1, there is included a mobile device 1 having either attached/connected thereto or included therein a 2D imaging sensor 2 and a structured sensor 3. The present embodiments are not limited to a mobile device 1 but may be any computing device capable of transferring information between sensors 2 and 3 and a network 20. The mobile device 1 is connected to the server 10 via the network. The server 10 is also connected to portal 11 and informatics 12.

The mobile device 1 may be a cellular/wireless enabled portable device with processing capacity and embedded 2D photo taking function via an imaging sensor 2. The mobile device 1 may include user interaction through touch screen, stylus, mouse, keyboard, or other means of input. The mobile device 1 may also have (3D) structure sensing functionality through connection with a structure sensor 3 connected to the mobile device 1 via an input/output port (e.g., a USB port) or other methods of connectivity such as via Bluetooth or near-field communication ("NFC"). The mobile device could be an Ipad™ by Apple Computer or a Galaxy Tab™ by Samsung or any other suitable mobile or tablet device having input/output capability.

The imaging sensor 2 may be a digital CCD sensor embedded or included with the mobile device 1 such as an iSight Camera™ by Apple Computer. The imaging sensor 2 may have any suitable resolution (such as 640×480 resolution, for example) and have any suitable number of pixels (such as 8 megapixels). However, the challenge with using a 2D camera to make a measurement of a wound is the lack of scaling information and distortion correction. In practice, photographers often place a reference object (ruler or object of known dimensions, such as a penny) in the same scene for pictures to be taken, so measurements can be derived later. However, this method requires the camera to be perpendicular to the measuring plane and is cumbersome and not accurate. However, several techniques have been developed that address this issue, including an embodiment in which the structure sensor 3 is included and is used in addition to the imaging sensor 2 as well as an embodiment in which the structure sensor 3 is absent and an on-screen guide is utilized together with information from the imaging sensor 2 to provide scaling information and distortion correction.

The structure sensor 3 may be a 3D imaging sensor such as the Occipital Structure Sensor™ developed by Occipital. Because of the spatial relationship of the imaging sensor 2 and the structure sensor 3 is known, 2D images taken from the imaging sensor 2 can be mapped to the 3D structure data acquired by the structure sensor 3. Thus, when obtaining information of a wound, images are obtained by both the imaging sensor 2 and the structure sensor 3. In an alternative embodiment, imaging information may be obtained from only the structure sensor 3 or from only the imaging sensor 2.

The structure sensor 3 enables accurate 3D measurement using the mobile device 1 without any further specialized device or any complicated process. The structure sensor 3 may be mounted to the mobile device 1 using a bracket. In addition to being implemented using the Occipital Structure Sensor™, the structure sensor 3 could also be implemented by a 3D stereo camera. Alternatively, the structure sensor 3 may be an apparatus that can be used in tandem with an existing mobile device to enable the capture of stereoscopic images, an apparatus that can be used with an existing camera to generate structured light (such as taught by "three-dimensional scanner for hand-held phones", J. Ryan Kruse, US20120281087A1), a miniaturized laser range scanner, or any potential apparatus that can be used in tandem with the mobile device 1 to capture the three dimensional information of the wound site.

The structure sensor 3 may be mounted to the mobile device 1 using, for example, a bracket. Alternatively, the structure sensor 3 may be external and not connected to the mobile device 1.

When obtaining the image information and 3D information using the imaging sensor 2 and the structure sensor 3, an on-screen guide can be provided which directs the image obtaining user to take the best possible picture. The on-screen guide can be displayed while the user is attempting to take a picture and will alert the user regarding whether the device is at the most optimal position for capturing the image. In addition, the guide can direct the user, for example, to more up or down or left or right in addition to information regarding lighting and tilt.

In addition to the 2D visual information and 3D measurements obtained by the imaging sensor 2 and the structure sensor 3, other physiological information may also be an important part of the clinical diagnosis. This other physiological information may be measured with additional apparatuses together with a mobile device 1. For instance, near-infrared thermal imaging can be used to detect heat to indicate infection, hyper spectral imaging techniques can be adapted to a mobile platform and be used for measuring tissue perfusion and necrosis, sensors can be used to detect and record odor, and other chemical sensors or bacterial detectors can be used in tandem with the current mobile platform. These additional sensors can be included in the same attachment as the structure sensor 3 or may be implemented as different structures. The additional sensors may also be implemented as external devices which connect to the mobile device 1 via wired or wireless communication.

The server 10 may be implemented locally within a doctor's office or at a hospital or may be implemented in the cloud via a server implementing a cloud service such as Amazon™ AWS. Any server handling private medical information may be implemented as a secured HIPAA compliant server. A HIPAA compliant server is one that is compliant with The Health Insurance Portability and Accountability Act of 1996 (HIPAA; Pub. L. 104-191, 110 Stat. 1936, enacted Aug. 21, 1996). The server may include a database or connected to a database in which information regarding the wound is stored. The server 10 may execute processing for analyzing the information obtained by the mobile device 1. The processing will be described in detail below.

The practitioner portal 11 is connected to the server 10 and is designed to provide information to the practitioner regarding the patient's wound. The wound information can be combined and integrated with a practitioner's existing electronic health record for the patient.

The informatics 12 provides a pathway for anonymized clinical data in the database to be accessed to support clinical research and health informatics to advance wound care.

Figure 2:
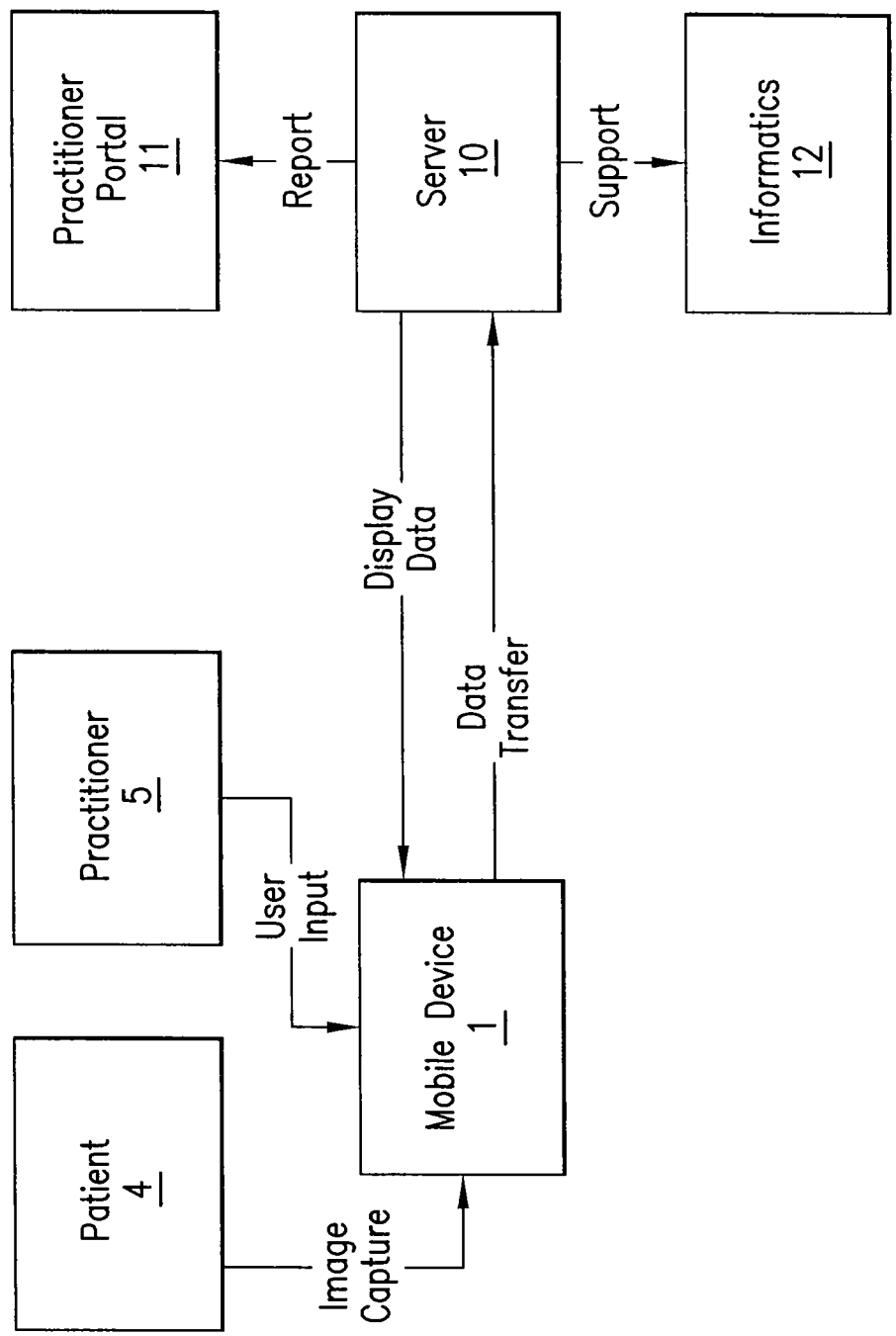
FIG. 2 illustrates another example of a system diagram according to one embodiment.

FIG. 2 illustrates a diagram illustrating the flow process of the system according to an embodiment. In the process, an image of the patient is captured by the mobile device 1, thereby generating image information. This information may include information from the imaging sensor 2 and the structure sensor 3 or other sensors as is discussed above.

Using the mobile device 1 and the associated imaging sensor 2 and the structure sensor 3 functionalities, 2D and 3D information of a wound is captured by the mobile device 1. Table 1 shown below provides an example of the 3D measurements obtained by the structure sensor 3.

TABLE 1

Width (cm)
Length (cm)
Circumference (cm)
Area (cm^2)
Depth (deepest, cm)
Volume (cm^3)
Segmentation: granulation, slough, necrotic
Percent (%)
Area (cm^2)
Measurement Date The practitioner 5 enters information via the mobile device to augment the imaging information obtained from the patient 4. In an alternative embodiment, the practitioner can enter the information via a different interface from the mobile device 1, which captures the imaging information.

Table 2 shows an example of the relevant clinical parameters obtained from the practitioner.

TABLE 2

| Location (figure) | Pain: | Co-morbidities |
|---|---|---|
| | At rest | Demographics |
| Type: | With Movement | |
| Traumatic | None | Current Treatment: |
| Pressure ulcer (Stage I/II/III/IV/unstageable) | Scale (0-10) | Topical Agent |
| Venous stasis | | Irrigation |
| Diabetic ulcer | Characteristics: | Negative Pressure |
| Surgical wound | Undermining (Yes/No, direction, length) | Secondary intention |
| Other | Tunneling (Yes/No, direction, length) | Debridement (Surgical/chemical) |
| Burn | Odor (Yes/No) | Other |
| Drainage: | Peri-Wound skin | Clinical |
| Serous | Edema | Blood glucose level |
| Serousanguineous | Erythema | Doppler signal |
| Purulent | Excoriation | Ankle brachial index |
| Amount (min/mod/large) | Maceration | |

The information found in tables 1 and 2 are transferred from the mobile device 1 (or other device) to the server 10 where the data is stored in a database together with previously generated wound parameters. Image analysis is then performed on the transferred information. The image analysis can be performed at the server 10 or, in an alternative embodiment, the image analysis can be performed locally on the mobile device 1.

Figure 3:
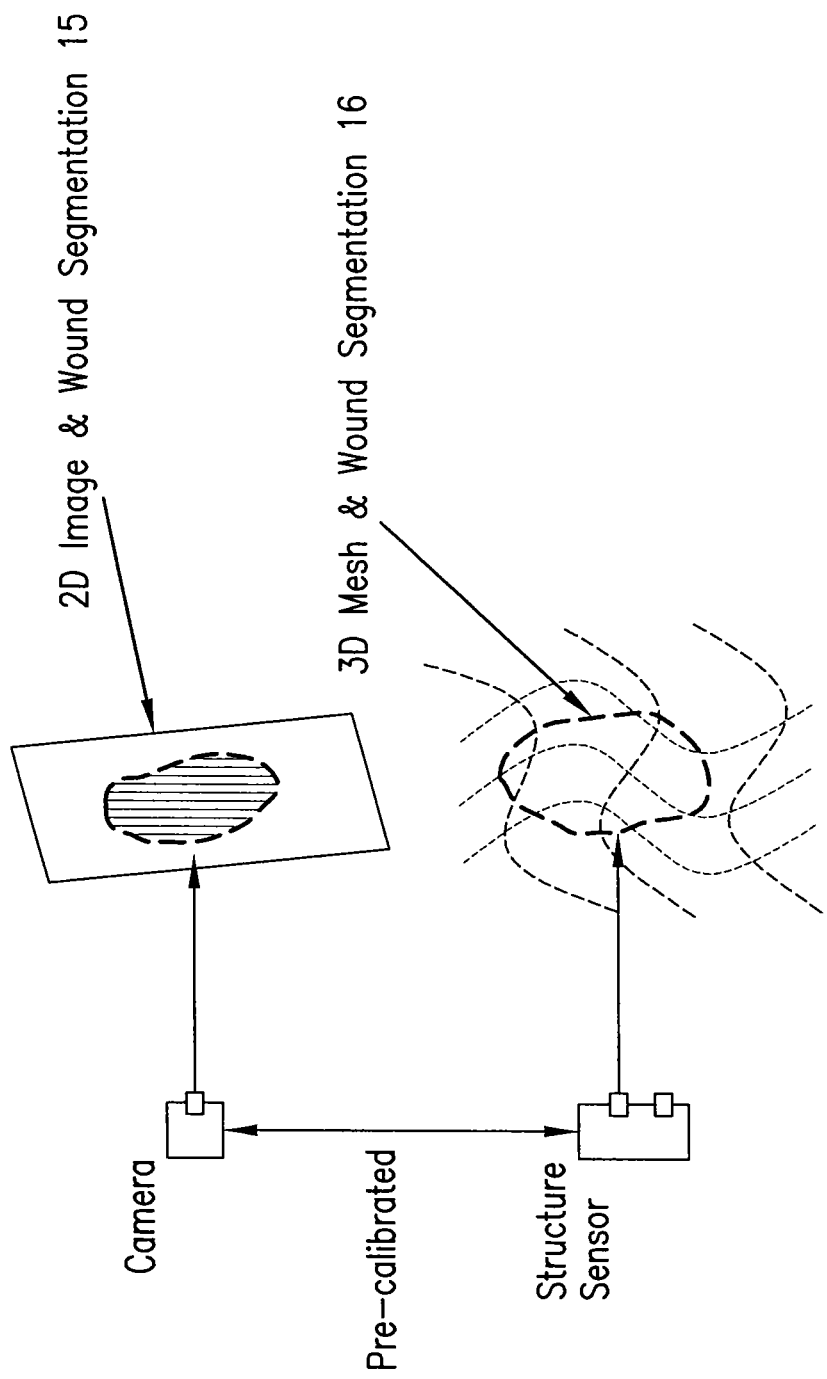
FIG. 3 illustrates an overview of the processing performed at the server using the information obtained from an imaging sensor and a structure sensor according to one embodiment.

FIG. 3 illustrates an overview of the processing performed at the server using the information obtained from the imaging sensor 2 and the structure sensor 3. In particular wound segmentation is performed using the 2D image information to obtain wound boundary information and the result is combined with the calculated 3D mesh information. Thus, the wound boundary segmented in the 2D image can be mapped into the 3D space, and the 3D measurements can be calculated from 3D structure data. The server 10 is not limited to performing processing using imaging data from the imaging sensor 2 or 3D data from the structure sensor 3. The server 10 may also perform the processing using saved images or images obtained remotely and forwarded to the server 10. As noted above, the image processing may also be performed on the mobile device 1 and in this instance, the image acquisition may be performed by using the built-in camera, downloading an image from the internet (dedicated server) or if available through an input/output interface such as a USB interface, using a USB flash drive.

Figure 4:
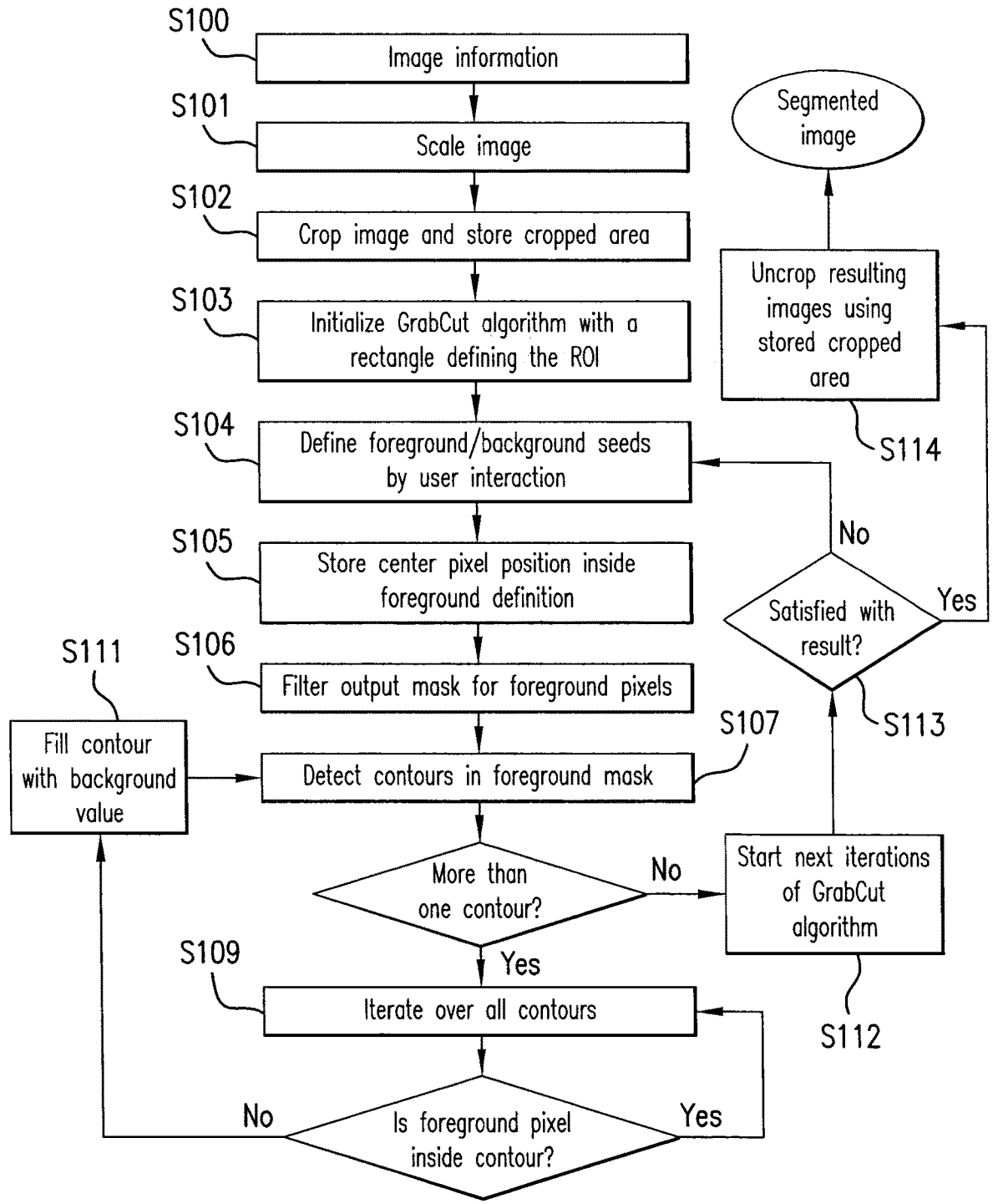
FIG. 4 illustrates a flow diagram showing the process for wound segmentation using 2D image information.

FIG. 4 shows a flow diagram showing the process for wound segmentation using the 2D image information. Image segmentation is performed with semi-automatic algorithm.

The processing of the image may include user or practitioner interaction during the image segmenting process. Alternatively, the processes may be performed without any user interaction such that any user input described in FIG. 4 would be replaced with automatic predictions or inputs.

In step S100, the 2D image information is obtained at the server 10 or at the mobile device 1. In step S101 the obtained image is scaled. As computation time depends on image size, in order to assure "real-time" (on-the-fly) segmentation, the image is scaled down. In step S102 the obtained image is cropped and the cropped area is stored. In particular, in order to have a closer look at the wound, the system zooms (e.g. ×2) into the image in order to focus on a predefined region in the center of the image. This assumes that the image places the wound approximately in the center of the image. The invisible part of the image defines the cropping region. Alternatively, the system could include a wound detection step at the cropping process to detect the location of wound for circumstances when the wound is not in the center of the image, for example. In step S103, the grab cut algorithm is initialized with a rectangle defining the region of interest (ROI). The ROI is defined at an offset of 20 pixels from the border. Alternatively, the ROI could be defined as any number of different shapes or wound locations or any offset number of pixels from the border.

Figure 5:
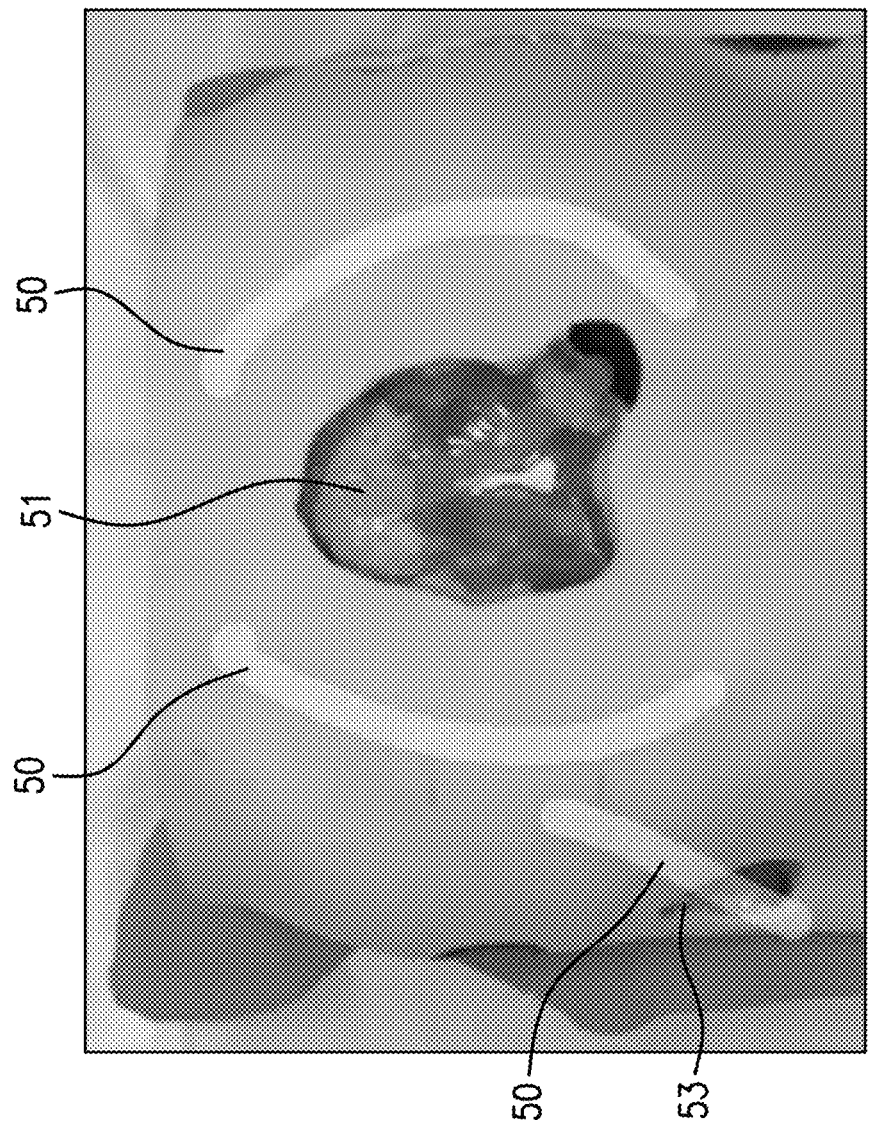
FIG. 5 illustrates an exemplary wound in which a foreground area corresponding to the wound and a background area have been designated according to one embodiment.

In step S104, the acquired image and directions for segmentation are shown to the user. Specifically, the user is shown the cropped and zoomed image. The user first indicates, parts of the object and parts of the background, or vice versa, using his/her finger or a stylus pen on a touchscreen, the mouse or a touchpad. Thus, the wound (foreground area) and the background are identified by user interaction. FIG. 5 illustrates an exemplary wound in which the foreground area 51 corresponding to the wound and the background area 50 have been designated by the user. As is illustrated in FIG. 5, the area 53 has been designated as a background area to ensure that this area is not detected as part of the wound. However, in an alternative embodiment, the system distinguishes this area from the main wound based on distance from the center of the picture and based on the existence of the other wound in the image and/or relative size between wounds. As is noted previously, the detection of the foreground and background portions of the image may be automatically performed at the server 10 or the mobile device 1. Given the diversity of wound shape, color, place, patients position, other objects inside the image (blanket, hand, etc.) detection of wounds is a difficult task requires smart algorithms like the grab cut algorithm which weighs homogeneity of the wound with border detection or machine learning methods which learn to classify pixel regions as wound or not wound. Both methods can be adjusted to work automatically without user interaction to provide an initial result. The inherent difficulty of segmenting wounds often requires that the segmentation process utilize post-processing which can be performed by the user to correct under and/or over segmentation or by another algorithm.

Described here are two exemplary algorithms that perform automatic wound image segmentation. Other algorithms could also be used. The first exemplary algorithm is grab cut based, where the user is shown the wound and an overlay of a rectangle in the center of the image. The user is asked to align the wound inside the rectangle and take an image. Everything outside the rectangle is considered as background and everything inside the rectangle is assigned with probabilities of being background or foreground. After initialization of the grab cut algorithm, an initial result will be calculated automatically and shown to the user.

The second exemplary approach is machine learning based, which requires the system, to learn, from several hundred images, background as skin, hand or other objects, and foreground as granulation, slough of eschar tissue, etc. After training the machine learning algorithm, a new image is divided into tiles and classified as background or foreground.

Both exemplary approaches also may give the user the possibility to correct for eventual errors and adjust the segmentation afterwards.

The further image processing starts automatically after or in response to the definition of both the object (foreground) and background, respectively. Alternatively, the further image processing is performed after the user provides an indication that the designation is complete.

The further image processing begins in step S105 in which the center pixel position inside the foreground definition is obtained. The grab cut algorithm can find several unconnected patches as wounds. When the user defines a region as wound, this indicates the user's intention to segment this region as wound and thereby use one pixel inside this region as the foreground. The system can then iterate over the wound patches and discard the patches not including the foreground pixel. The iteration starts after S107, depending on if more than one contour has been found.

In step S106, the output mask is filtered for foreground pixels. After each iteration, the grab cut algorithm outputs a mask defining the background as 0, the foreground as 1, likely background as 2, and likely foreground as 3. This mask is filtered for only foreground pixels. All other assignments (0,2,3) are replaced by 0. The result is a binary mask which contains 1 for foreground pixels and 0 for background pixels.

In step S107, the contours in the foreground mask are detected and it is determined whether there is more than one contour in the foreground mask. When more than one contour is found, in step S109, the system iterates over all contours and detects whether each contour includes a foreground pixel. As described above, the result of one segmentation iteration can be several foreground patches on the image. In S107 the binary mask is used to detect the contours of these patches. In step S109, it is determined whether the foreground pixel is inside of one of the contours, and if so then this contour is defined as the wound of interest otherwise if the foreground pixel is not inside the contour, then this area is determined to be not the wound.

For each contour that does not include a foreground pixel, the contour is filled with the background value in step S111. To ensure that only one contour enters S112, the system detects again for contours in the modified binary mask and addresses any additional contours by iterating again over the contours. In the case that only one contour is left, the flow proceeds to step S112.

In step S112, the next iteration of the grab cut algorithm is performed. This process generates an initial segmentation that delineates the object border using a prominent polygon overlay.

In step S113, it is determined whether the user is satisfied with the result. If not, the flow returns to step S104 whereby the user can refine the segmentation by using additional indications for object or background or both until satisfied.

In step S114, the resulting images are uncropped using the stored cropped area. The resulting image is output as a segmented image.

This semi-automatic segmentation algorithm can be implemented using the grab cut algorithm as described by Carsten Rother, Vladimir Kolmogorov, and Andrew Blake. 2004. *"GrabCut": interactive foreground extraction using iterated graph cuts. In ACM SIGGRAPH* 2004 *Papers* (*SIGGRAPH* '04), Joe Marks (Ed.). ACM New York, N.Y., USA, 309-314. DOI=10.1145/1186562.1015720, herein incorporated by reference or another segmentation algorithm such as a graph cut algorithm. In this process, the user specifies the seed regions for wound and non-wound areas using simple finger swipes on a touchscreen. The segmentation result is displayed in real-time, and the user also has the flexibility to fine-tune the segmentation if needed. This algorithm requires minimal supervision and delivers a very fast performance.

Figure 6:
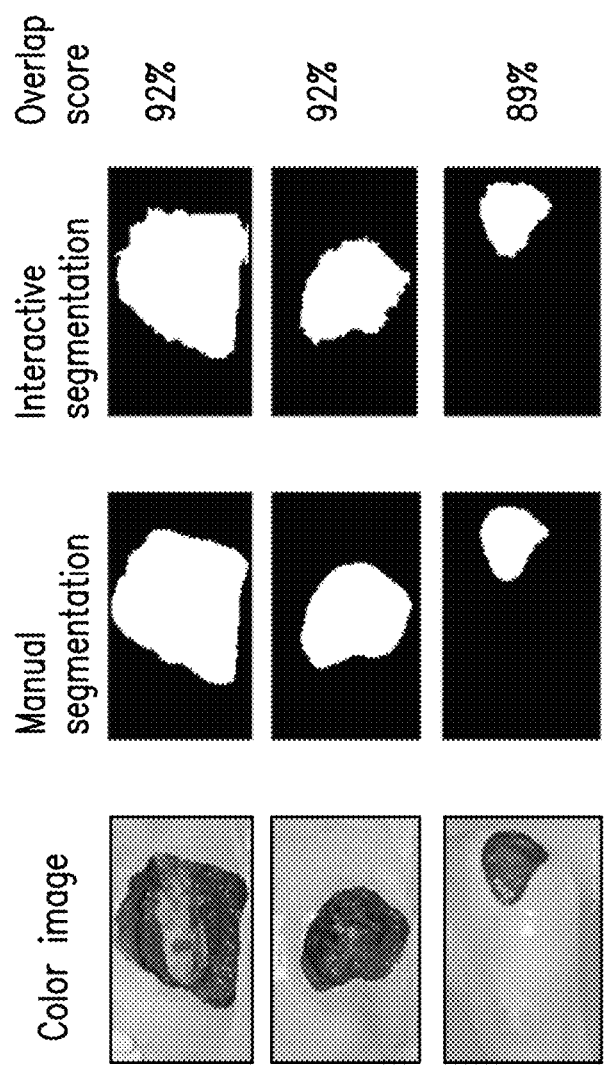
FIG. 6 illustrates an implementation example according to one embodiment.

Exemplary evidence of the effectiveness of the image segmentation was obtained using a selection of 60 wound images which were used for validation. Five clinicians were asked to trace wound boundaries using a stylus on a windows tablet running the Matlab program. The results were compared against the present wound border segmentation process using a normalized overlap score. As shown in FIG. 6, the present implementation of the segmentation algorithm showed very good overlap with the experts' manual segmentations (overlap score of around 90%). The algorithm also reduced task time from around 40 seconds to <4 seconds.

Figure 7:
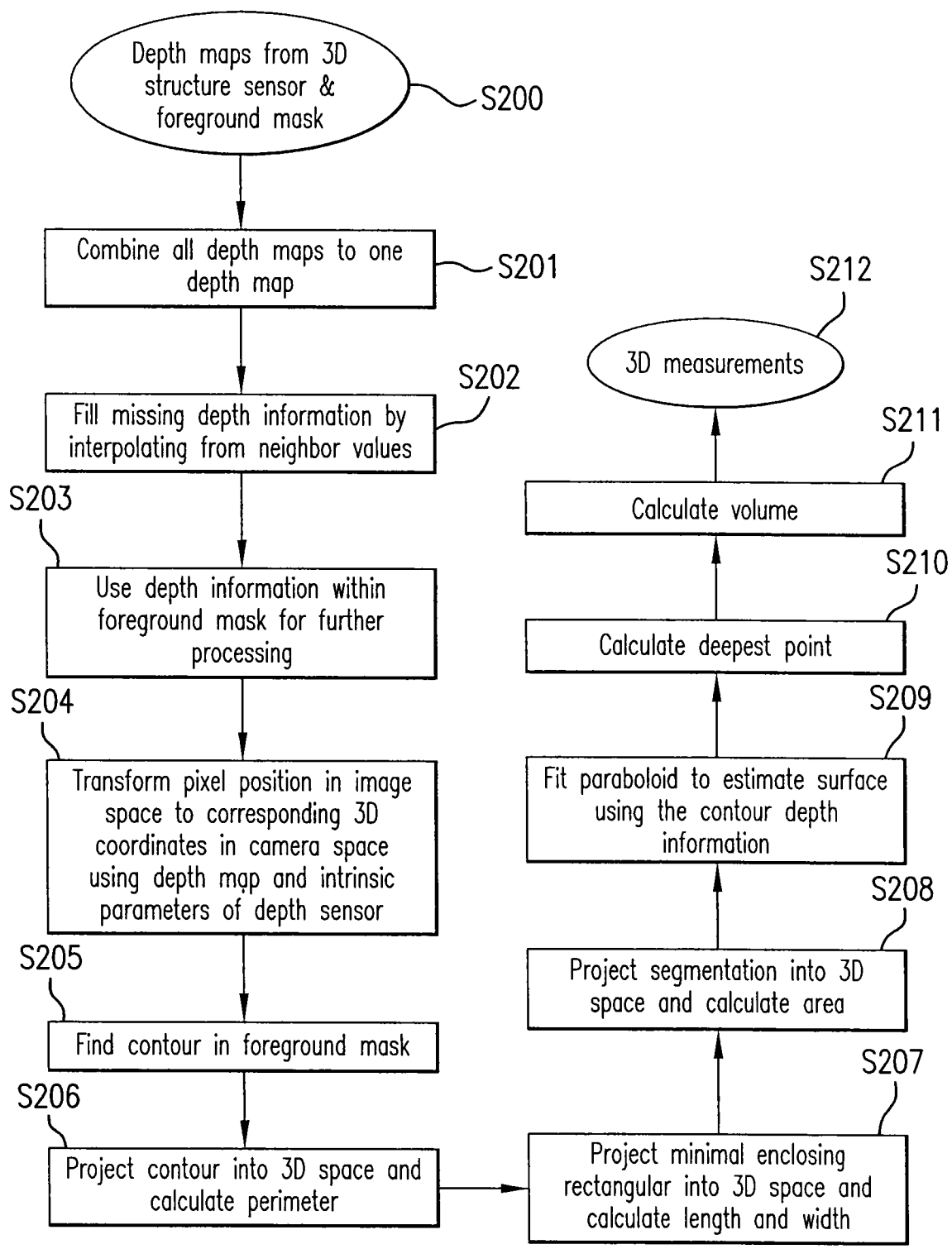
FIG. 7 illustrates a flow diagram showing the process for computing the 3D measurements from the structure sensor data and the obtained segmented image.

FIG. 7 shows a flow diagram showing the process for computing the 3D measurements from the structure sensor 3 data and the obtained segmented image from the process shown in FIG. 4. The structure sensor 3 data is topology information that provides information about the medical injury (wound). In particular, once the wound border is segmented in the 2D color image, the segmentation can be mapped into 3D space, enabling the 3D wound model to be extracted. Dimensions such as width and length can be calculated by applying Principal Component Analysis (PCA) to the point cloud. Alternatively, the rotated rectangle of the minimum area enclosing the wound can be found. The width and the length of the rectangle define the extent of the wound i.e. width and length, respectively. The perimeter can be computed by adding the line segments delineating the wound boundary. For area, volume, and depth, a reference plane is first created using paraboloid fitting to close the 3D wound model. This reference plane follows the anatomical shape of the surrounding body curvature, representing what normal skin surface should be without the wound. The area of the wound can be calculated as the surface area of the reference plane enclosed within the wound boundary. The volume is the space encapsulated by the reference plane and the wound surface; depth is the maximum distance between these two surfaces. These automated algorithms can be implemented, for instance, in OpenCV.

Figure 8:
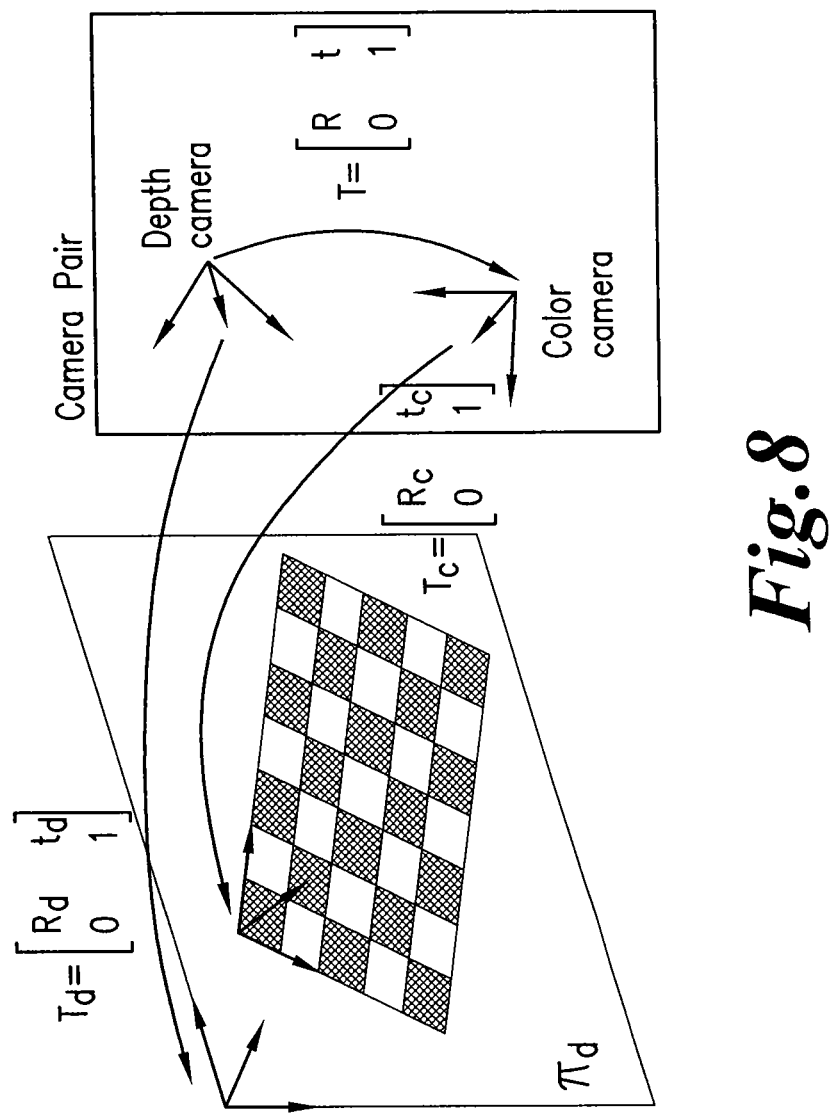
FIG. 8 illustrates an example of the calibration of the structure sensor with the imaging sensor.

Another important aspect is the aligning of the structure sensor 3 with the imaging sensor 2. In one embodiment, these two sensors have a rigid 6DOF transform between them because of the fixed mounting bracket. In this embodiment, a chessboard target and a stereo calibration algorithm, such as is found in OpenCV, is used to determine the transformation. To do so, the individual sensors are calibrated using a zero distortion model for the structure sensor 3, and a distortion and de-centering model for the imaging sensor 2. Then, with all internal sensor parameters fixed (including focal length), the external transformation is calculated between the two sensors using a stereo calibration function such as the OpenCV stereoCalibrate function. As shown in FIG. 8, both sensors observe the same planer surface, allowing the computation of the extrinsic calibration, similar to that of calibrating a Kinect depth camera with its own RGB camera. Alternatively, automated calibration method of a color camera with a depth camera can be used. With good calibration, the segmented wound border in the color image can be more accurately mapped onto the 3D structure data, and accurate wound dimensions can be computed.

In step S200 of FIG. 7, depth maps obtained by the structure sensor 3 and the foreground mask and corresponding to the segmented image, are obtained. The foreground mask is a binary image with the same size as the color image but encodes the wound as foreground by assigning 1 to pixels belonging to the wound and 0 otherwise (background).

In step S201, the all depth maps are combined into a single depth map. This step is performed to ensure a uniform depth map. In particular, depth maps are very noisy. Therefore some depth values in the depth map are missing. By storing several consecutive depth maps, it is possible to fill in the gaps by combining all the depth maps to one depth map. Although this step reduces the majority of missing depth values, some gaps can still remain. S202 applies another method to fill in gaps using the depth values of neighboring pixels.

In step S202, any missing depth information is filled by interpolating from neighboring values.

Figure 9:
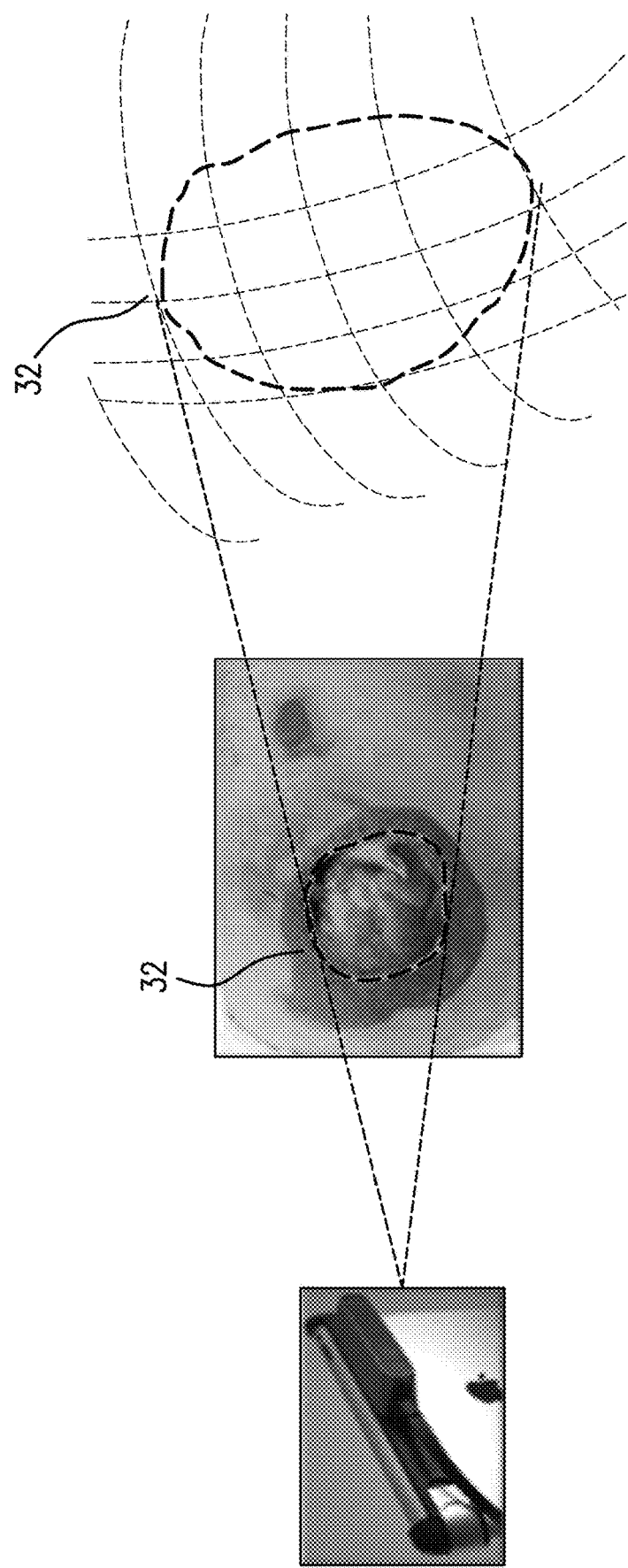
FIG. 9 illustrates that the foreground mask is applied to the depth data such that only the depth information within the area is obtained.

In step S203, the depth information within the area, which is represented by the foreground mask is used for further processing. For instance, FIG. 9 illustrates that the foreground mask 32 is applied to the depth data such that only the depth information within the area is obtained.

In step S204, the pixel position in the 2D image space is transformed to corresponding 3D coordinates in camera space using the depth map and intrinsic parameters of the structure sensor 3.

In step S205, the contour within the foreground mask area is determined and in step S206, the determined contour is projected into 3D space whereby the perimeter is calculated. This perimeter is the total length of the wound border (like circumference of a circle), but in 3D space.

In step S207, the minimal enclosing rectangle is projected into 3D space and the length and width of the wound are calculated. Thus, S206 calculates the perimeter of the wound and S207 calculates the maximum length and width of the wound.

In step S208, the segmentation (foreground mask) is projected into 3D space and the area is calculated.

In step S209, a parabolic shape is fit to estimate the surface using the contour depth information.

In step S210, the deepest point within the wound is calculated and in step S211, the volume of the wound is calculated.

In step S212, width, length, perimeter, area, volume, depth (deepest) and segmentation of the wound, determined from the previous steps, are output.

Figure 10:
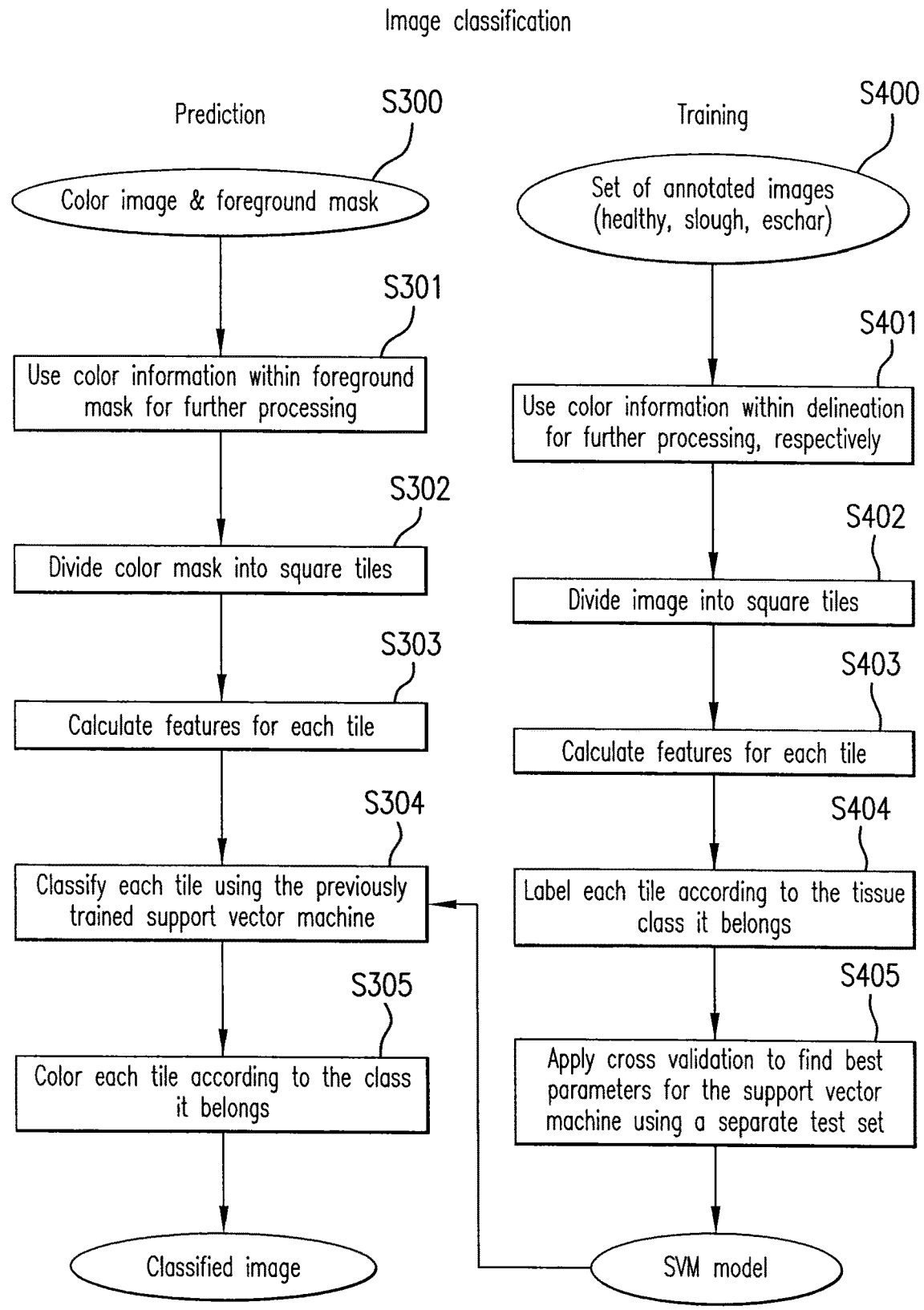
FIG. 10 illustrates the process for classifying the tissue in the wound.
Figure 11E:
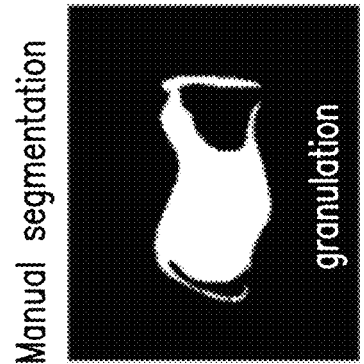
FIGS. 11A-F illustrate a comparison between manual and automatic segmentation.
Figure 11F:
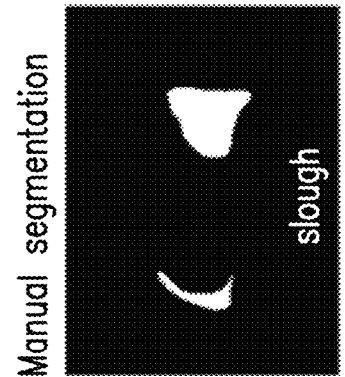
Figure 11C:
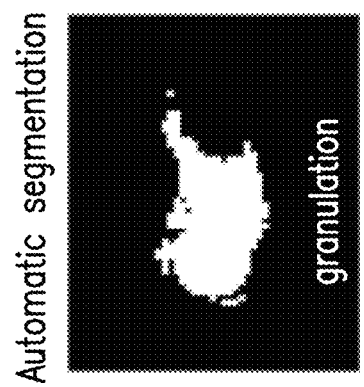
Figure 11D:
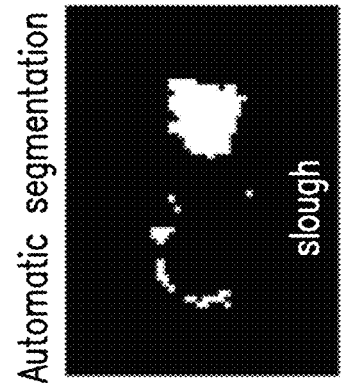
Figure 11A:
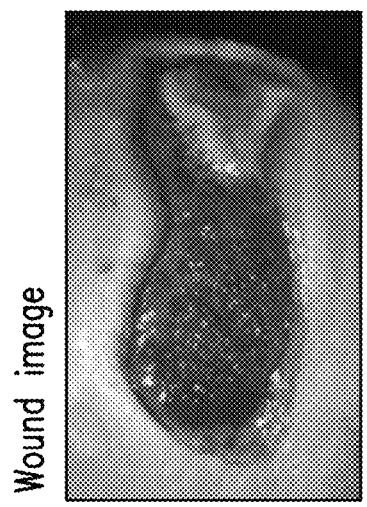
Figure 11B:
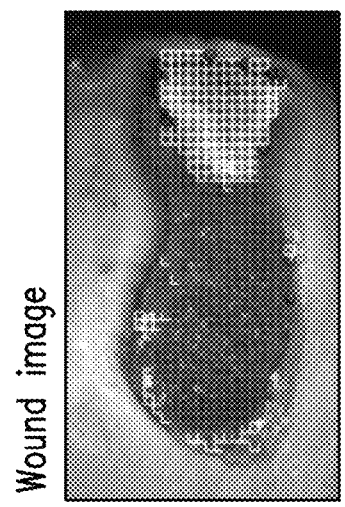

The server 10 may also perform wound tissue classification processing. Alternatively, this processing can also be performed at the mobile device 1. FIG. 10 illustrates the process for classifying the tissue in the wound. In this process, after extracting the wound border, the wound tissue can be classified into granulation, and/or slough, and/or eschar tissues. A tile-based multi-class Support Vector Machine (SVM) classifier can be used to automate the task. The SVM may be trained on 100 images of different wounds, each providing hundreds of tiles to learn the features for the classifier. Cross validation and grid search can be used to optimize the learning process and the quality of generalization. Experimental testing showed good overlap (Overlap Score >80%) between manual and automatic segmentation as is shown in FIGS. 11A-F. FIG. 11A shows the original wound image, FIG. 11B shows the overlay with classification algorithm output, FIG. 11C shows automatic classification for granulation and FIG. 11D shows automatic classification for slough tissues. FIG. 11E shows manual classification by an expert for granulation and FIG. 11F shows manual classification by an expert for slough tissues.

In step S300 of FIG. 10, the color image obtained by the image sensor 2 is obtained along with the foreground mask.

In step S301, the color information within the area of the color image corresponding to the foreground mask is obtained.

In step S302, the color information with the mask is divided into tiles, such as square tiles. Other shaped tiles may also be used. In step S303, the features are calculated for each tile. The features are extracted elements. In particular, in one example, when an image is given in RGB color format, the may be converted from RGB to, HSV, LAB and/or grayscale formats and following features extracted: a) average and standard deviation of H, S values in each tile, respectively; b) average and standard deviation of L, A, and B values in each tile, respectively; and c) average and standard deviation of gray values, respectively. In step S304, each the is classified using a trained support vector machine. The training process is shown in steps S400-S406.

In step S400, a set of images are obtained that annotate areas of healthy, slough, and/or eschar tissue in the wound. These images are then further processed in step S401 so that the respective color information, within the annotated area, are linked to the respective annotation. In step S402, the images are each divided in to square tiles. The features noted above are then calculated for each tile in step S403. In step S404, each tile is labeled according to the tissue class to which it belongs. In steps S405, cross validation is applied to find the best parameters for the support vector machine using a separate test set. In step S406 a SVM model is generated.

The model generated in step S406 is used in step S304 to classify each tile. In step S305, each tile is colored with a predetermined color according to the class it belongs such that each class has a different color. In step S306, the classified image having the colors highlighted thereon is output.

When the processing is performed at the server 10, the server 10 transfers data back to the mobile device 1 for display to the practitioner. The data may also be transmitted is a different device in place of the mobile device 1.

Figure 12:
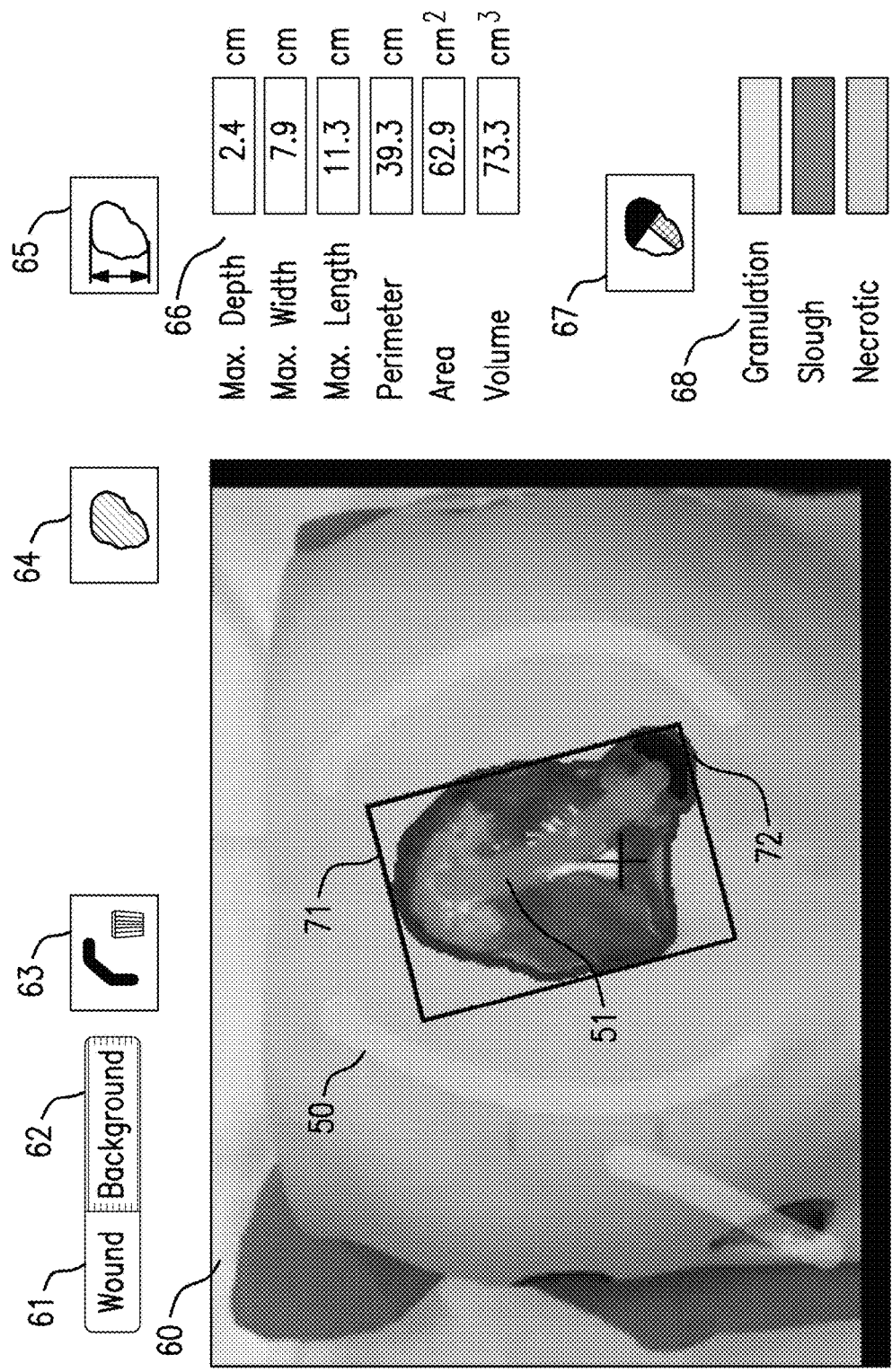
FIG. 12 illustrates an example of the system interface according to one embodiment.

FIG. 12 illustrates an example of the interface provided to the practitioner. The information populating this interface is either generated within the mobile device 1 or sent to the mobile device 1 or an alternative device from the server 10.

The interface displays the color image 60 and provides the user with the ability to mark the wound 51 by selecting toggle 61 and to mark the background 50 by selecting toggle 62. Button 63 enables the user to erase markings. Once the markings 50 and 51 are placed, the user may select the segmentation button 64, which initiates the processing shown in FIG. 4. Once this processing is complete, the wound border information is returned to the interface to be displayed as border 72.

The user may then select the measurement button 65 which initiates the processing shown in FIG. 7. Once this processing is complete and the result of the processing obtained, a minimal enclosing rectangle 71 is displayed and the wound measurements 66 are shown.

The user may also select the wound tissue classification button 67 which classifies different portions of the wound based on the classes 68 using different colors. Once the button 67 is selected the processing shown in FIG. 10 is performed. The result of the processing is overlaid onto the wound.

The data generated by the server 10, in addition to being forwarded to the mobile device 1, is also stored in a database. The database may be local to the server 10 or in remote or cloud location. As the data may be medically sensitive, the data may be stored in encrypted form and/or in a protected way to ensure that privacy is maintained.

The data generated by the server 10 or locally at the mobile device 1 can be stored in the database. This data includes the wound image and the relevant clinical data both manually entered and automatically generated using the image processing methods. Using historical data in the database for a particular patient, the patient's wound healing progress can be analyzed to output parameters similar to those listed on Table 3 shown below. Thus, this information together with other visual features of the wound can then be integrated to support clinical decisions. From the database, clinical information, including the information listed on Tables 1, 2, and 3, can be accessed for reporting on the wound management or practitioner portal 11. The information stored in the database can be incorporated into a patient's existing electronic health record managed by the practitioner. Using the management portal 11, a practitioner, who is a physician, a nurse, a researcher, or anyone with the proper authorization and credentials, can access the information to provide wound management in a HIPAA compliant manner. This portal can also be used for care coordination.

TABLE 3

| % Change (/week, vs. last measurement, vs. specific measurement date): |
| --- |
| Area |
| Volume |
| Depth (deepest) |
| Tissue classification |
| Absolute Change (/week, vs. last measurement, vs. specific measurement date): |
| Area |
| Volume |
| Depth (deepest) |
| Tissue Classification |

Benchmark scope: individual, practice, institution, region, national

Similarly, anonymized clinical data in the database can be accessed via an informatics interface 12 to support clinical research and health informatics to advance wound care.

The present embodiments provide significant advantages. For example, the present system is able to effectively ensure that wounds are measured uniformly. The uniformity of the system makes consulting and cross-referencing much more feasible. Another advantage of the system is that the audit process for documentation with health insurers and Medicare/Medicaid fiscal intermediaries is significantly enhanced in the event of a chart audit for services rendered. The stored images prove treatment plans, skin substitute applications and progression (or lack) of healing. Another advantage of this system is the ability to supplement internal organizational audits regarding wound benchmark healing programs.

Additionally, the mobile device 1 could further include educational materials for patients and reference materials for care providers, such as guide for classifying wounds and front-line treatment modalities, current CPT coding guidelines for skin substitutes, updates on pharmaceuticals relevant to wound management/infection control, and the ability to secure link to existing electronic health record (EHR) systems.

To support collaboration between care givers, the system is also able to enable a patient to grant access to medical history data when being transferred between different facilities, and to allow the care team to collectively contribute to patient medical records along with the patient themselves through self-monitoring and self-reporting.

The present embodiments can also be applied to other applications besides wound measurement.

In another embodiment, the present embodiments can be also used as a preventive measure for population with higher risk of developing chronic wounds, such as diabetic patients who are prone to diabetic foot ulcer, an immobilized patient that is prone to developing pressure ulcers, and a patient with peripheral vascular diseases. A main reason for developing ulcers is the poor blood supply leading to ischemic tissue, which eventually develops into necrosis and ulcers. The present embodiments incorporated with multi-spectrum imaging or other advanced imaging technology and/or an image analysis algorithms, can be used to assess the blood supply or blood perfusion on body surfaces. For instance, a band-pass, band-stop, low-pass, or high-pass filter can be used to take images under different wavelengths of light, which can be used to analyze the blood oxygen contents in the superficial layers of the skin, similar to the technology used in pulsoxymetry. For instance, a light source in the near-infrared range with two different wavelengths can be used. The light filter together with the light source can be combined together and outfitted to an existing camera phone to enhance its multi-spectrum imaging capability for measuring blood perfusion.

In yet another embodiment, the present embodiments can be used to monitor conditions in the ears, nose, throat, mouth, and eyes. To enhance the visual images, an auxiliary light source could be used. A light guide could also be used to take a picture of a location that is hard to reach, or in some cases or situations, stabilization and magnification could also be used. These features can be developed to be outfitted to an existing mobile device to allow the patient to take a better quality picture, which enables computers to extract clinical information more accurately, and enables care providers to better monitor disease progression and to detect and address risk for complications.

In yet another embodiment, the present embodiments can be used to monitor for a disease condition that has visible bulging, swelling, or protruding feature on body surface, including but not limited to peripheral vascular disease, skin lumps, hernia, and hemorrhoids. The size and shape of those lesions are of clinical relevance and can be easily measured and tracked with the present embodiments.

In yet another embodiment, the present embodiments can be used for plastic reconstructive surgery or weight loss regimen, where changes of body shape can be measured and documented.

In yet another embodiment, the present embodiments can be used to monitor patient excretion, such as defecation and urination, the visual characteristics of which might have clinical relevance.

In yet another embodiment, the present embodiments can be used to monitor patient caloric intake based on volume and identification of food groups for a number of medical conditions in which both fluid and solid intake must to be monitored.

In summary, the present disclosure may be applied to methods and system for chronic disease management based on patient's self-monitoring and self-reporting using mobile devices. Specifically, the disclosure utilizes a camera-enabled mobile device (with or without special add-on device, such as stereo camera, structured light, multi-spectrum light imager, or other light source or light guide) to obtain visual information for the site of interest, including but not limited to ostomy, wound, ulcer, skin conditions, dental, ear, nose, throat, and eyes. Alternatively, this task could be achieved by utilizing a webcam enabled laptop, or a combination of a camera and a computer system. Visual information, including but not limited to the size, shape, color, hue, saturation, contrast, texture, pattern, 3D surface, or volumetric information, are of great clinical value in monitoring disease progression. The present embodiments disclose a techniques of using camera-enabled mobile device (with or without additional apparatus to enhance, improve, or add imaging capabilities) to acquire images, analyze, and extract clinical relevant features in the acquired image, which are later transmitted to a remote server. Alternatively, all the image analysis and feature recognition could be performed on the remote server site. Medical professionals or a computer-automated algorithm can access those patient data and determine the risk of deteriorating conditions, early warning signs for complications, or patients' compliance to treatments. In one embodiment, computer automation will serve as the first line of defense. This system is able to screen all patient data for early warning signs. Once a risk is identified, a care provider and/or patients can be altered when certain indication is out of normal range or trending unfavorably. Care providers can then evaluate the case, either confirm or dismiss the alert and take appropriate action to address the alert, including communicating with patients, adjusting therapy, or reminding patient to adhere to treatment. Based on the clinical information extracted from the image, patient communications, and patient's disease profile, and provider's treatment plans, the system can be used to place targeted advertisement and make product recommendations.

In an alternative embodiment, the depth information and the image information can be obtained by a single imaging device or sensor. In this embodiment, the imaging device or sensor is able to capture depth information of the wound in addition to capturing an image of the wound. In addition, it is also possible to determine the distance of portions of the image such as the wound based on auto-focusing information. For instance, by identifying the distance differences between the wound and the background it is possible to determine depth information of the wound.

At least certain portions of the processing described above, such the processes shown in FIGS. 4, 7 and 10, for example, can be implemented or aided by using some form of embedded or external computer having at least one microprocessor or by using a circuitry/processing circuitry. Any of the above described processes may be performed using a computer or circuitry or processing circuitry. As one of ordinary skill in the art would recognize, the computer processor can be implemented as discrete logic gates, as an Application Specific Integrated Circuit (ASIC), a Field Programmable Gate Array (FPGA) or other Complex Programmable Logic Device (CPLD). An FPGA or CPLD implementation can be coded in VHDL, Verilog or any other hardware description language and the code can be stored in an electronic memory directly within the FPGA or CPLD, or as a separate electronic memory. Further, the electronic memory can be non-volatile, such as ROM, EPROM, EEPROM or FLASH memory. The electronic memory can also be volatile, such as static or dynamic RAM, and a processor, such as a microcontroller or microprocessor, can be provided to manage the electronic memory as well as the interaction between the FPGA or CPLD and the electronic memory.

Alternatively, the computer processor can execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions can be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OSX and other operating systems known to those skilled in the art.

Figure 13:
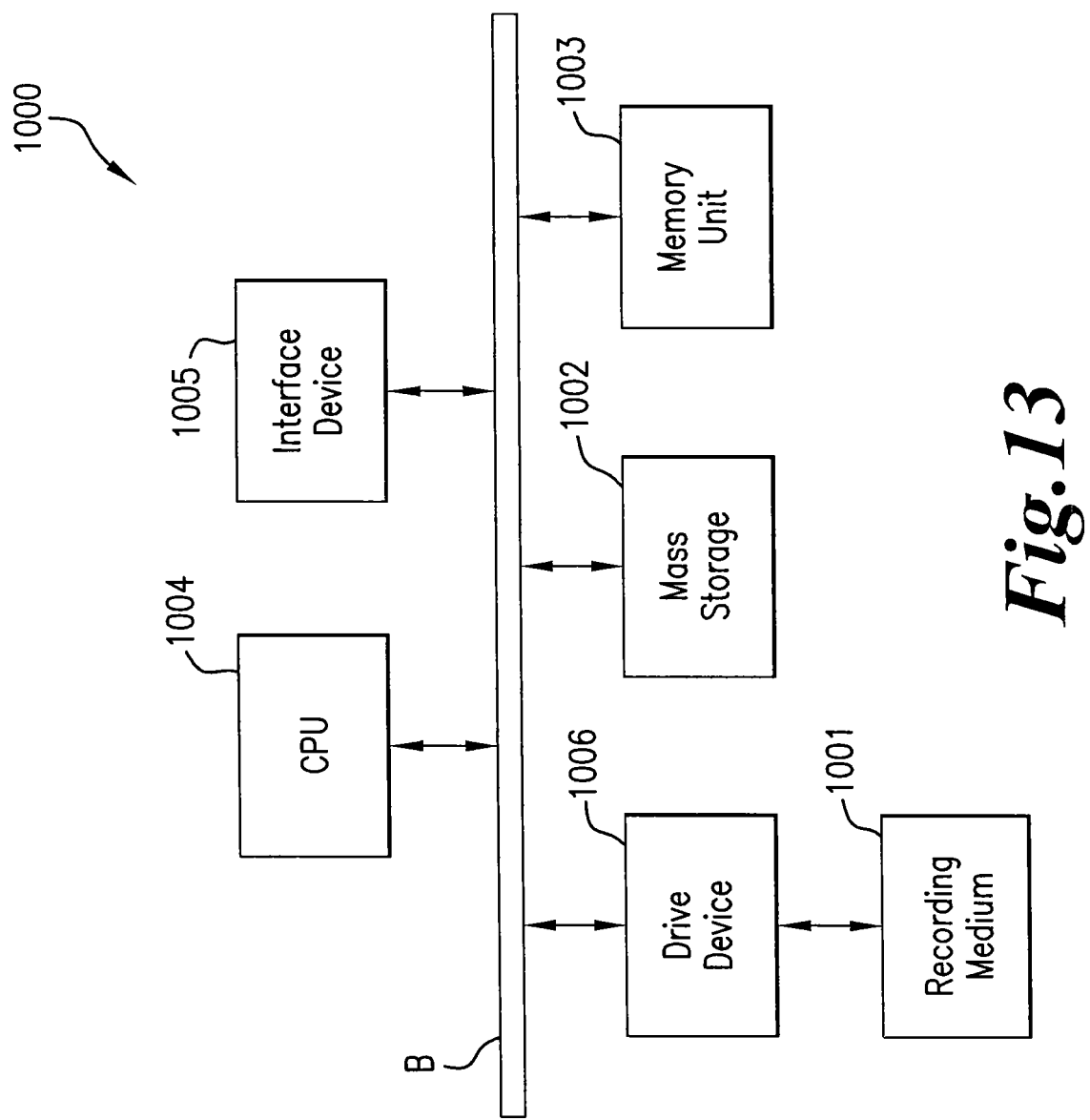
FIG. 13 illustrates an exemplary computing system according to one embodiment.

In addition, certain features of the embodiments can be implemented using a computer-based system (FIG. 13). The computer 1000 includes a bus B or other communication mechanism for communicating information, and a processor/CPU 1004 coupled with the bus B for processing the information. The computer 1000 also includes a main memory/memory unit 1003, such as a random access memory (RAM) or other dynamic storage device (e.g., dynamic RAM (DRAM), static RAM (SRAM), and synchronous DRAM (SDRAM)), coupled to the bus B for storing information and instructions to be executed by processor/CPU 1004. In addition, the memory unit 1003 can be used for storing temporary variables or other intermediate information during the execution of instructions by the CPU 1004. The computer 1000 can also further include a read only memory (ROM) or other static storage device (e.g., programmable ROM (PROM), erasable PROM (EPROM), and electrically erasable PROM (EEPROM)) coupled to the bus B for storing static information and instructions for the CPU 1004.

The computer 1000 can also include a disk controller coupled to the bus B to control one or more storage devices for storing information and instructions, such as mass storage 1002, and drive device 1006 (e.g., read-only compact disc drive, read/write compact disc drive, compact disc jukebox, and removable magneto-optical drive). The storage devices can be added to the computer 1000 using an appropriate device interface (e.g., small computer system interface (SCSI), integrated device electronics (IDE), enhanced-IDE (E-IDE), direct memory access (DMA), or ultra-DMA).

The computer 1000 can also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer 1000 can also include a display controller coupled to the bus B to control a display, for displaying information to a computer user. The computer system includes input devices, such as a keyboard and a pointing device, for interacting with a computer user and providing information to the processor. The pointing device, for example, may be a mouse, a trackball, or a pointing stick for communicating direction information and command selections to the processor and for controlling cursor movement on the display. In addition, a printer can provide printed listings of data stored and/or generated by the computer system.

The computer 1000 performs at least a portion of the processing steps of the invention in response to the CPU 1004 executing one or more sequences of one or more instructions contained in a memory, such as the memory unit 1003. Such instructions can be read into the memory unit from another computer readable medium, such as the mass storage 1002 or a removable media 1001. One or more processors in a multi-processing arrangement can also be employed to execute the sequences of instructions contained in memory unit 1003. In alternative embodiments, hard-wired circuitry can be used in place of or in combination with software instructions. Thus, embodiments are not limited to any specific combination of hardware circuitry and software.

As stated above, the computer 1000 includes at least one computer readable medium 1001 or memory for holding instructions programmed according to the teachings of the invention and for containing data structures, tables, records, or other data described herein. Examples of computer readable media are compact discs, hard disks, magneto-optical disks, PROMs (EPROM, EEPROM, flash EPROM), DRAM, SRAM, SDRAM, or any other magnetic medium, compact discs (e.g., CD-ROM), or any other medium from which a computer can read.

Stored on any one or on a combination of computer readable media, the present invention includes software for controlling the main processing unit 1004, for driving a device or devices for implementing the invention, and for enabling the main processing unit 1004 to interact with a human user. Such software can include, but is not limited to, device drivers, operating systems, development tools, and applications software. Such computer readable media further includes the computer program product of the present invention for performing all or a portion (if processing is distributed) of the processing performed in implementing the invention.

The computer code elements on the medium of the present invention can be any interpretable or executable code mechanism, including but not limited to scripts, interpretable programs, dynamic link libraries (DLLs), Java classes, and complete executable programs. Moreover, parts of the processing of the present invention can be distributed for better performance, reliability, and/or cost.

The term "computer readable medium" as used herein refers to any medium that participates in providing instructions to the CPU 1004 for execution. A computer readable medium can take many forms, including but not limited to, non-volatile media, and volatile media. Non-volatile media includes, for example, optical, magnetic disks, and magneto-optical disks, such as the mass storage 1002 or the removable media 1001. Volatile media includes dynamic memory, such as the memory unit 1003.

Various forms of computer readable media can be involved in carrying out one or more sequences of one or more instructions to the CPU 1004 for execution. For example, the instructions can initially be carried on a magnetic disk of a remote computer. An input coupled to the bus B can receive the data and place the data on the bus B. The bus B carries the data to the memory unit 1003, from which the CPU 1004 retrieves and executes the instructions. The instructions received by the memory unit 1003 can optionally be stored on mass storage 1002 either before or after execution by the CPU 1004.

The computer 1000 also includes a communication interface 1005 coupled to the bus B. The communication interface 1004 provides a two-way data communication coupling to a network that is connected to, for example, a local area network (LAN), or to another communications network such as the Internet. For example, the communication interface 1005 can be a network interface card to attach to any packet switched LAN. As another example, the communication interface 1005 can be an asymmetrical digital subscriber line (ADSL) card, an integrated services digital network (ISDN) card or a modem to provide a data communication connection to a corresponding type of communications line. Wireless links can also be implemented. In any such implementation, the communication interface 1005 sends and receives electrical, electromagnetic or optical signals that carry digital data streams representing various types of information.

The network typically provides data communication through one or more networks to other data devices. For example, the network can provide a connection to another computer through a local network (e.g., a LAN) or through equipment operated by a service provider, which provides communication services through a communications network. The local network and the communications network use, for example, electrical, electromagnetic, or optical signals that carry digital data streams, and the associated physical layer (e.g., CAT 5 cable, coaxial cable, optical fiber, etc). Moreover, the network can provide a connection to a mobile device such as laptop computer, or cellular telephone.

In the above description, any processes, descriptions or blocks in flowcharts should be understood as representing modules, segments or portions of code which include one or more executable instructions for implementing specific logical functions or steps in the process, and alternate implementations are included within the scope of the exemplary embodiments of the present advancements in which functions can be executed out of order from that shown or discussed, including substantially concurrently or in reverse order, depending upon the functionality involved, as would be understood by those skilled in the art.

While certain embodiments have been described, these embodiments have been presented by way of example only, and are not intended to limit the scope of the inventions. Indeed, the novel methods, apparatuses and systems described herein can be embodied in a variety of other forms; furthermore, various omissions, substitutions and changes in the form of the methods, apparatuses and systems described herein can be made without departing from the spirit of the inventions. The accompanying claims and their equivalents are intended to cover such forms or modifications as would fall within the scope and spirit of the inventions.

The invention claimed is:

1. A system for determining characteristics of a medical injury, comprising:
one or more imaging sensors that obtain imaging information and topology information of an area of interest, the imaging information including two-dimensional information of objects in the area of interest and the topology information including three-dimensional information of objects in the area of interest; and
processing circuitry configured to
determine, using the imaging information, a two-dimensional boundary of an injury portion within the imaging information, wherein the two-dimensional boundary of the injury portion is a locus of points enclosing the injury portion within the imaging information,
map only the locus of points enclosing the injury portion within the imaging information to a corresponding locus of points within the topology information based on a fixed geometric relationship between the one or more imaging sensors,
generate a three-dimensional point cloud based on the corresponding locus of points within the topology information, the three-dimensional point cloud defining the medical injury, and
determine characteristics of the medical injury based on the three-dimensional point cloud, wherein
the characteristics include a depth of the medical injury, and the characteristics are displayed for assessment of the medical injury.

2. The system according to claim 1, wherein the processing circuitry is further configured to
designate a representative background portion of the area of interest from the imaging information,
designate a representative injury portion of the area of interest from the imaging information, and
determine the two-dimensional boundary of the injury portion within the imaging information based on the designated representative background portion and the designated representative injury portion.

3. The system according to claim 2, wherein the processing circuitry is further configured to designate the representative injury portion of the area of interest from the imaging information based on user input or pixel characteristic differences.

4. The system according to claim 2, wherein the processing circuitry is configured to determine the two-dimensional boundary of the injury portion within the imaging information by detecting contours in the designated representative injury portion of the area of interest.

5. The system according to claim 2, wherein the processing circuitry is configured to determine the two-dimensional boundary of the injury portion within the imaging information by detecting contours in the designated representative injury portion of the area of interest and iterating over all contours.

6. The system according to claim 1, wherein the processing circuitry is further configured to
classify the medical injury by dividing the injury portion into tiles, calculating a measure of central tendency for imaging values of each tile, and classifying each tile using injury type information generated by a previously trained machine learning classifier, the injury type information including healthy tissue, slough tissue, and eschar tissue.

7. The system according to claim 6, wherein the previously trained machine learning classifier generates the injury type information using processing circuitry configured to, for a set of annotated images,
divide each image into tiles,
calculate a measure of central tendency for imaging values of each tile,
designate each tile according to an injury type, and
apply cross-validation using a separate test set.

8. The system according to claim 1, wherein the characteristics of the medical injury further include maximum depth, average depth, width, and length of the medical injury or include perimeter, area, and volume of the medical injury.

9. The system according to claim 1, wherein the processing circuitry is configured to determine the two-dimensional boundary of the injury portion within the imaging information by utilizing an automatic image segmentation algorithm.

10. The system according to claim 1, wherein the objects are portions of a body of a patient suffering the medical injury.

11. The system according to claim 1, wherein the one or more imaging sensors includes two or more sensors that simultaneously acquire the imaging information and the topology information.

12. The system according to claim 1, wherein the one or more imaging sensors include a structure sensor that projects light from the structure sensor.

13. The system according to claim 1, wherein the processing circuitry is further configured to
combine multiple topology maps included in the topology information to generate a single combined topology map as the topology map.

14. The system according to claim 1, wherein the processing circuitry is further configured to
generate other topology information representing a surface of the area of interest in an absence of the medical injury, the other topology information being generated using a part of the topology information that is outside of the medical injury to extrapolate the other topology information,
determine a volume of the medical injury using a difference between the other topology information and the topology information, and
determine a maximum depth of medical injury using a maximum of the difference between the other topology information and the topology information.

15. A device for determining characteristics of a medical injury, comprising:
processing circuitry configured to
obtain imaging information and topology information of an area of interest, the imaging information and the topology information having been acquired using one or more imaging sensors, the imaging information including two-dimensional information of objects in the area of interest and the topology information including three-dimensional information of objects in the area of interest,
determine, using the imaging information, a two-dimensional boundary of an injury portion within the imaging information, wherein the two-dimensional boundary of the injury portion is a locus of points enclosing the injury portion,
map only the locus of points enclosing the injury portion within the imaging information to a corresponding locus of points within the topology information based on a fixed geometric relationship between the one or more imaging sensors,
generate a three-dimensional point cloud based on the corresponding locus of points within the topology information, the three-dimensional point cloud defining the medical injury, and
determine characteristics of the medical injury based on the three-dimensional point cloud, wherein
the characteristics include a depth of the medical injury, and the characteristics are displayed for assessment of the medical injury.

16. The device according to claim 15, wherein the processing circuitry is further configured to
designate a representative background portion of the area of interest from the imaging information,
designate a representative injury portion of the area of interest from the imaging information, and
determine the two-dimensional boundary of the injury portion within the imaging information based on the designated representative background portion and the designated representative injury portion.

17. The device according to claim 16, wherein the processing circuitry is further configured to designate a representative injury portion of the area of interest from the imaging information based on user input or pixel characteristic differences.

18. The device according to claim 16, wherein the processing circuitry is configured to determine the two-dimensional boundary of the injury portion within the imaging information by detecting contours in the designated representative injury portion of the area of interest.

19. The device according to claim 16, wherein the processing circuitry is configured to determine the two-dimensional boundary of the injury portion within the imaging information by detecting contours in the designated representative injury portion of the area of interest and iterating over all contours.

20. The device according to claim 15, wherein the processing circuitry is further configured to
classify the medical injury by dividing the injury portion into tiles, calculating a measure of central tendency for imaging values of each tile, and to classifying each tile using injury type information generated by a previously trained machine learning classifier, the injury type information including healthy tissue, slough tissue, and eschar tissue.

21. The device according to claim 20, wherein the previously trained machine learning classifier generates the injury type information using processing circuitry configured to, for a set of annotated images,
divide each image into tiles,
calculate a measure of central tendency for imaging values of each tile,
designate each tile according to an injury type, and
apply cross-validation using a separate test set.

22. The device according to claim 15, wherein the characteristics of the medical injury further include maximum depth, average depth, width, and length of the medical injury or perimeter, area and volume of the medical injury.

23. The device according to claim 15, wherein the processing circuitry is configured to determine the two-dimensional boundary of the injury portion within the imaging information by utilizing a grab cut algorithm.

24. A method for determining characteristics of a medical injury, comprising:
obtaining, from one or more imaging sensors, imaging information and topology information of an area of interest, the imaging information including two-dimensional information of objects in the area of interest and the topology information including three-dimensional information of objects in the area of interest;
determining, using processing circuitry and using the imaging information, a two-dimensional boundary of an injury portion within the imaging information, wherein the two-dimensional boundary of the injury portion is a locus of points enclosing the injury portion;
mapping, using the processing circuitry, only the locus of points enclosing the injury portion within the imaging information to a corresponding locus of points within the topology information based on a fixed geometric relationship between the one or more imaging sensors;

generating, using the processing circuitry, a three-dimensional point cloud based on the corresponding locus of points within the topology information, the three-dimensional point cloud defining the medical injury; and determining, using the processing circuitry, characteristics of the medical injury based on the three-dimensional point cloud.

25. The method according to claim 24, wherein the method further comprises designating, using the processing circuitry, a representative background portion of the area of interest from the imaging information, designating, using the processing circuitry, a representative injury portion of the area of interest from the imaging information, and determining, using the processing circuitry, the two-dimensional boundary of the injury portion within the imaging information based on the designated representative background portion and the designated representative injury portion, wherein the characteristics include a depth of the medical injury, and the characteristics are displayed for assessment of the medical injury.

26. The method according to claim 25, wherein the method further comprises designating, using the processing circuitry, a representative injury portion of the area of interest from the imaging information based on user input or pixel characteristic differences.

27. The method according to claim 25, wherein the method further comprises determining using the processing circuitry, the two-dimensional boundary of the injury portion within the imaging information by detecting contours in the designated representative injury portion of the area of interest.

28. The method according to claim 25, wherein the method further comprises determining, using the processing circuitry, the two-dimensional boundary of the injury portion within the imaging information by detecting contours in the designated representative injury portion of the area of interest and iterating over all contours.

29. The method according to claim 24, wherein the method further comprises classifying, using the processing circuitry, the medical injury by
dividing the injury portion into tiles,
calculating a measure of central tendency for imaging values of each tile, and
classifying each tile using injury type information generated by a previously trained machine learning classifier, the injury type information including healthy tissue, slough tissue, and eschar tissue.

30. The method according to claim 29, wherein the previously trained machine learning classifier generates the injury type information by, for a set of annotated images,
dividing, using processing circuitry, each image into tiles,
calculating, using the processing circuitry, a measure of central tendency for imaging values of each tile,
designating, using the processing circuitry, each tile according to an injury type, and
applying, using the processing circuitry, cross-validation using a separate test set.

31. The method according to claim 24, wherein the characteristics of the medical injury further include maximum depth, average depth, width, and length of the medical injury or include perimeter, area and volume of the medical injury.

32. The method according to claim 24, wherein the method further comprises
determining, using the processing circuitry, the two-dimensional boundary of the injury portion within the imaging information by utilizing a grab cut algorithm.

33. The method according to claim 24, wherein the medical injury is a wound.

34. A system for determining characteristics of a medical injury, comprising:
one or more imaging sensors that obtain imaging information and topology information of an area of interest, the imaging information including two-dimensional information of objects in the area of interest and the topology information including three-dimensional information of objects in the area of interest; and
processing circuitry configured to
determine, using the imaging information, a two-dimensional boundary of an injury portion within the imaging information, wherein the two-dimensional boundary of the injury portion is a locus of points enclosing the injury portion,
map the locus of points enclosing the injury portion within the imaging information to a corresponding locus of points within the topology information based on a fixed geometric relationship between the one or more imaging sensors,
generate, from the topology information, a three-dimensional point cloud based on the corresponding locus of points within the topology information, the three-dimensional point cloud defining the medical injury, and
determine characteristics of the medical injury based on the three-dimensional point cloud, wherein
the characteristics include a depth of the medical injury, and the characteristics are displayed for assessment of the medical injury.

* * * * *